(12) United States Patent
Maaskamp et al.

(10) Patent No.: US 8,801,653 B2
(45) Date of Patent: Aug. 12, 2014

(54) SURGICAL APPARATUS AND METHODS ASOCIATED THEREWITH

(76) Inventors: Armand Maaskamp, Coto De Caza, CA (US); Alex Urich, Rancho Santa Margarita, CA (US)

(*) Notice: Subject to any disclaimer, the term of this patent is extended or adjusted under 35 U.S.C. 154(b) by 426 days.

(21) Appl. No.: 12/802,370

(22) Filed: Jun. 4, 2010

(65) Prior Publication Data
US 2010/0312170 A1 Dec. 9, 2010

Related U.S. Application Data

(60) Provisional application No. 61/217,809, filed on Jun. 4, 2009, provisional application No. 61/275,735, filed on Sep. 2, 2009.

(51) Int. Cl.
*A61M 1/00* (2006.01)

(52) U.S. Cl.
USPC .............................................. 604/30; 604/35

(58) Field of Classification Search
CPC . A61M 1/0031; A61M 1/0058; A61M 1/008; A61F 9/00745
USPC ................. 604/30, 33, 35; 606/107
See application file for complete search history.

(56) References Cited

U.S. PATENT DOCUMENTS

| | | | |
|---|---|---|---|
| 5,106,367 A | 4/1992 | Ureche et al. | |
| 5,167,620 A | 12/1992 | Ureche et al. | |
| 6,599,271 B1 | 7/2003 | Easley | |
| 7,727,179 B2 * | 6/2010 | Barrett | 604/27 |
| 7,914,482 B2 | 3/2011 | Urich et al. | |
| 8,092,427 B2 | 1/2012 | Urich et al. | |
| 2002/0128560 A1 * | 9/2002 | Urich | 600/500 |
| 2006/0100570 A1 | 5/2006 | Urich et al. | |
| 2006/0173426 A1 | 8/2006 | Urich et al. | |
| 2011/0137233 A1 | 6/2011 | Urich et al. | |
| 2011/0257614 A1 | 10/2011 | Urich et al. | |

OTHER PUBLICATIONS

Barry S. Seibel; Phacodynamics Mastering the Tools and Techniques of Phacoemulsification Surgery;Second Edition: Copyright 1995; pp. 2, 3, 6, 7, 12, 16-23, 54, and 55; SLACK Incorporated;USA.

* cited by examiner

Primary Examiner — Theodore Stigell
(74) Attorney, Agent, or Firm — J. Bruce Hoofnagle

(57) ABSTRACT

A surgical apparatus 10, used in a phaco procedure, includes a filter assembly 44/44a for near, or complete, elimination of air bubbles in an aspiration line of an aspiration system 38. The apparatus 10 includes a suppressor 110, which, during an aspiration mode of operation, maintains a fluid flow rate at 50 cc/min, and, upon an occlusion breaking free, dynamically decreases the fluid flow rate from a high surge rate to the rate at 50 cc/min. The apparatus 10 includes facility for operating in a reflux mode to direct unrestricted fluid flow through the aspiration line of the aspiration system 38.

23 Claims, 9 Drawing Sheets

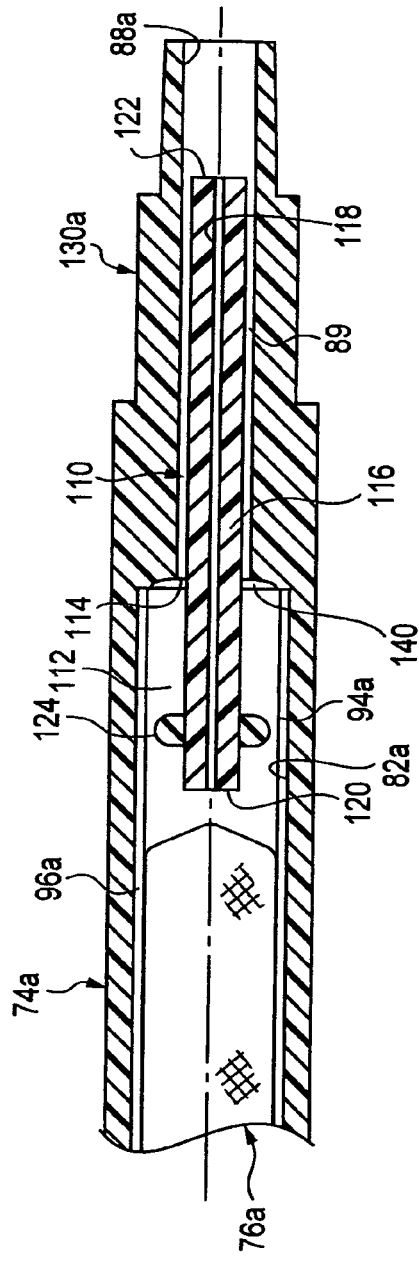
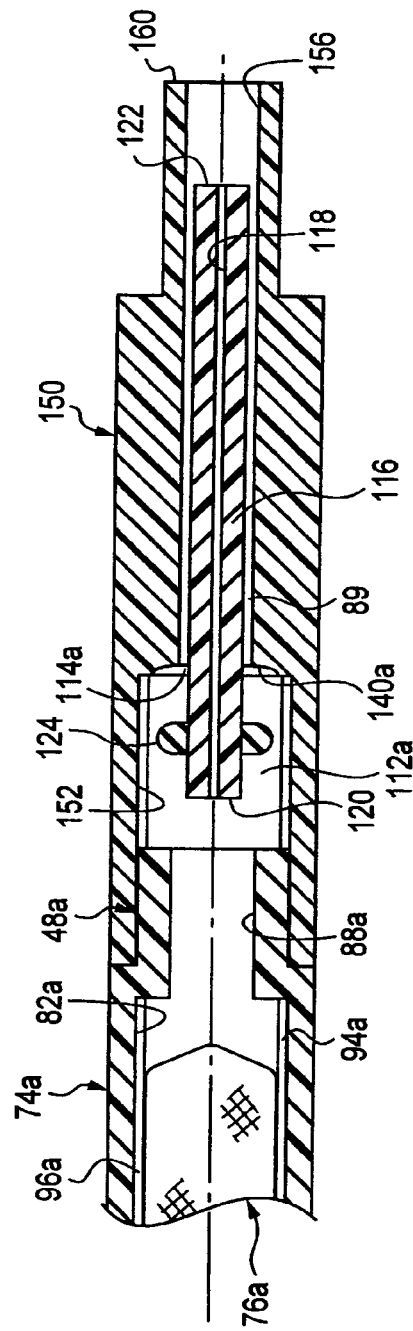
FIG. 9
FIG. 10

SURGICAL APPARATUS AND METHODS ASOCIATED THEREWITH

This application claims the benefit of U.S. Provisional Application No. 61/217,809, filed on Jun. 4, 2009, and U.S. Provisional Application No. 61/275,735, filed on Sep. 2, 2009, both of which are incorporated herein by reference thereto.

FIELD OF THE INVENTION

This invention relates to surgical apparatus and to methods associated therewith, and, in particular, relates to surgical apparatus, which includes an aspiration system, having a filter assembly and a dynamic surge suppressor, for use in surgical procedures, and further relates to methods associated with such surgical apparatus.

BACKGROUND OF THE INVENTION

It has been disclosed in the past, at least to a limited extent, that in certain surgical procedures conducted within a body cavity, such as, for example, a phacoemulsification procedure, a lens capsule, located in an anterior chamber of a human eye, is broken into particles and residual debris (all hereinafter referred to as "the particles"), must be continuously withdrawn or flushed from the site of the surgery. During the surgical procedure, an irrigation fluid is fed, for example, by gravity or positive pumping, into the cavity, and the irrigation fluid and the broken lens particles contained therein are withdrawn, as an aspiration fluid, from the cavity by a pumping action, which develops an aspiration fluid flow and a negative or vacuum pressure. Thereafter, the particles are segregated from the aspiration fluid, by filtering, and the particle-free filtered fluid is then transferred to a waste depository, or fluid-collection chamber, at a site remote from the site of the surgery.

When performing a phacoemulsification procedure, it is essential to maintain a positive pressure within the anterior chamber of the eye, which contains the lens capsule. A negative pressure within the chamber may cause the cornea to collapse. In order to maintain a positive pressure within the anterior chamber, the flow of the irrigation fluid is maintained at a rate which is at least slightly greater than the flow rate of the aspiration fluid.

The following example of a surgical apparatus, which includes an aspiration system, is used in a phacoemulsification procedure regarding the removal of cataract tissue and the affected lens of the eye, in the form of the particles. The principle of operation of the below-described phacoemulsification surgical apparatus could be used in other surgical procedures, such as, for example, knee and shoulder surgery, where removal of particles from the surgical site is critical Apparatus used in previous phacoemulsification surgical procedures include a hand piece, which is held and manipulated by a surgeon during the procedure. The hand piece supports a hollow ultrasonically-driven cannula having an open free-end tip at an inlet end of the hollow cannula. The surgeon maneuvers the hand piece to insert the cannula tip through an incision in the patient's cornea and into the patient's eye. The cannula tip is then moved by the surgeon adjacent and/or into engagement with a cataractous lens of the eye to break the lens into the particles.

As the lens is broken into the particles, an irrigation fluid is fed by gravity, or pumped, into the eye, through an irrigation line, to initiate a process of flushing the particles from the eye. An aspiration system is employed to continue the flushing action of the now particle-laden fluid through and out of the eye in the form of an aspiration fluid. An aspiration line of the aspiration system provides a conduit for the aspiration fluid, and includes an inlet opening formed by the open free-end tip of the cannula, the hollow cannula, a first aspiration tube, a filter-containing housing, a second aspiration tube, and an outlet end of the line. The aspiration system further includes an aspiration pump, which facilitates the flow of the aspiration fluid from the eye in an aspiration direction, i.e., away from the eye and toward the outlet end of the aspiration line, by developing a fluid-flow stream and a relatively low vacuum pressure in the aspiration line.

The aspiration pump is typically one of three known types of fluid pumps, namely a peristaltic pump, a venturi pump, or a diaphragm pump. For purposes of explanation, the above-described apparatus uses a peristaltic pump, which includes a circular rotating pump head having a periphery adjacent, and spaced from, a circular wall of a stationary pump housing. Radially-spaced rollers are mounted on the periphery of the head for orbiting movement about an axial center of rotation of the head. An axially-stationary, flexible aspiration tubing is located about the periphery of the head, and between the head and the circular wall of the housing, for passage of fluid through the tubing. As the head is rotated, each successive orbiting roller pinches successive portions of the stationary tubing against the circular wall of the housing, thereby pushing fluid forward within the tubing, in the direction of rotation of the head. Collectively, the orbiting rollers urge the fluid in a continuous flow through the aspiration line, at a generally steady and controllable flow rate, from the eye toward fluid-collection chamber.

A surgical apparatus which can be used to effect the above-described phacoemulsification procedure, is disclosed in U.S. Patent Application Publication No. 2006/0173404, which was published on Aug. 3, 2006.

It is well known that air is a highly compressible medium, and when the air bubbles generated during the operation of, the aspiration system are subjected to the vacuum pressure, the air bubbles expand under the vacuum pressure, and contract when the vacuum pressure is lowered. In addition, the air bubbles may coalesce, thereby forming large pockets of air within the aspiration system. In this manner, the presence of air within the aspiration system interferes with the efficient operation of the system, and could stall the operation thereof.

If a large volume of air is present in the system, it is feasible that the required vacuum pressure to sustain a delicate balance between the incoming flow rate of the irrigation fluid to the patient's eye, and the outgoing flow rate of the aspiration fluid and particles from the eye, could be undesirably altered, with catastrophic results to the patient's eye, and inefficient operation of the surgical procedure. Consequently, the minimization, if not the elimination, of air within the aspiration system is critically important.

In an effort to minimize the impact of air within the aspiration system, prior to the aspiration process, a purging of the aspiration line may, and should, be conducted to eliminate any air within the system. Notwithstanding the purging process, during the aspiration process, troublesome air bubbles may develop within the system, particularly in the cannula, the first aspiration tube, the filter housing, and the juncture connections of these components of the system.

One apparatus which considers the air-bubble concern is disclosed in U.S. Pat. No. 6,599,271 (the '271 patent"), which issued on Jul. 29, 2003, where an ophthalmic flow converter includes two flow paths, a first path for fluid flow and a second path for air flow.

As described in the '271 patent, the first path includes a first hydrophilic filter for filtering particles from an aspirated fluid, whereafter the filtered fluid is passed through a restrict opening of a manually-adjustable variable orifice, and then to a waste-storage cassette. Air, contained in the pre-filtered fluid of an aspiration line, is directed through a second hydrophilic filter in the second path, which bypasses the first filter and the variable orifice, and thereafter rejoins the filtered fluid.

As further described in the '271 patent, until the first filter becomes fully wetted by the incoming unfiltered fluid, air will pass through the first filter as well as the second filter. Thereafter, when the first filter becomes fully wetted, the first filter tends not to pass air, with the air then being directed through the second filter, to bypass the first filter.

In one embodiment of the ophthalmic flow converter described in the '271 patent, and illustrated in FIGS. 2 through 5 thereof, the converter is attached directly to an output end of an ultrasound needle within a hand piece, which is smaller in diameter than the converter. This difference in the diameters is necessitated by the design of a converter with two flow paths and two filters, and presents a potentially unwieldy combination for handling of the hand piece during an aspiration process.

In addition, the air which enters the first flow path prior to the first filter becoming fully wetted, may remain undesirably in the first path as the aspiration process continues. Further, even after the first filter becomes fully wetted, the first filter only tends not to pass air. Also, any air bubbles developed in the fluid subsequent to the fluid passing through the wetted filter, remain with the fluid and cannot be rerouted through the second filter.

Thus, there is a need for a surgical apparatus which, during a surgical procedure, will minimize, if not eliminate, the negative effects of air developed within an aspiration line of the surgical apparatus, during the flow of fluid in the aspiration line while operating in an aspiration mode.

In a phacoemulsification procedure, it is critical that a perfect fluid balance be maintained within the surgical apparatus wherein the flow rate of the aspiration fluid is always lower than the flow rate of the infused irrigation fluid, as noted above. If this balance is not maintained, a negative pressure may develop in the eye whereby the cornea and/or the entire eye will move and sometimes collapse. This condition can occur when a full occlusion blocks the opening of the free-end tip of, or occurs within, the hollow cannula, or elsewhere within the aspiration line, whereby the aspirated particle-laden fluid ceases to flow.

Typically, during normal operation of the surgical apparatus, a relatively low level of vacuum pressure, such as, for example, 20 mmHg to 50 mmHg, is developed by the peristaltic pump to facilitate the unoccluded suctioning of the particles, with the peristaltic pump is also simultaneously pumping the aspiration fluid to move the suctioned particles from the eye and farther into the aspiration line. If an occlusion occurs, for example, at the inlet opening of the free end tip of the cannula, the particle-laden fluid ceases to flow in the aspiration line, even though the peristaltic pump continues to operate. With the fluid ceasing to flow, and the pump continuing to operate, the vacuum pressure begins to increase.

During this period of occlusion, the vacuum pressure generated by the vacuum pump should be allowed to increase significantly, typically to 250 mmHg, or even higher to a range of 400 mmHg to 500 mmHg, in order to allow the increased vacuum pressure to quickly suction the occlusion into the hollow cannula, and farther into the aspiration line, and thereby allow the aspiration system to attempt to return to the perfect fluid balance. The presence of the increased vacuum pressure, when the occlusion breaks free, causes a potentially hazardous surge, or high flow rate, of the aspiration fluid within the aspiration line.

Such a surge of the aspiration fluid can lead to transient aspiration flow rates through the aspiration line that substantially exceed the flow rate of the irrigation fluid into the eye. This causes a sub-ambient pressure to be momentarily applied to surrounding tissue of the eye. The sub-ambient pressure condition may cause (1) an undesirable collapse of the anterior chamber of the eye, (2) undesirable damage to the posterior aspect of the lens capsule of the eye, and/or (3) undesirable movement of endothelium cells, which are critical to normal functions of the cornea, away from the cornea and towards the free-end tip of the cannula. On the other hand, independent of the formation of the above-noted occlusion, an irrigation-fluid flow rate, which is too high, may also move the endothelium cells away from the cornea, or undesirably cause the cells to be aspirated out of the eye.

The apparatus of the '271 patent includes the variable restrictive orifice, the restrictive opening of which is located in the sole path of flow of the fluid in the aspiration line thereof, during an aspiration mode as well as during a reflux mode. A manually-operable adjustment device is provided for selectively restricting the opening of the orifice, prior to the initiation of the phaco procedure, to limit the rate of flow of the fluid through the sole path of the aspiration line during an entire phaco procedure. The illustration of FIG. 5 of the '271 patent shows the opening of the orifice in a nearly closed position, which, as noted in the patent, is representative of the adjustment when the control device is being used. Further, after an air purging process, and before initiation of the phaco procedure, the desired flow rate for the phaco procedure may be obtained by using the manually-operable adjustment device to establish the desired size of the restrictive opening. This desired size of the restrictive opening remains unchanged during the entire phaco procedure in the aspiration mode.

The apparatus of the '271 patent is used to set the restrictive opening to a single size for the entire phaco procedure, and does not present any opportunity for adjusting the size of the restrictive opening during the procedure.

In U.S. Patent Application Publication No. 2002/0128560 ("the '560 publication"), which was published on Sep. 12, 2002, a fluid flow restrictor, having a fixed restriction passage is fixedly coupled to a filter housing to restrict the pressure drop within an aspiration system. The fluid flow restrictor of the '560 publication does not show any facility for adjusting the size of the restriction at any time during an aspiration procedure.

As disclosed in U.S. Pat. No. 5,106,367, which issued on Apr. 21, 1992, and companion U.S. Pat. No. 5,167,620, which issued on Dec. 1, 1992, an aspiration system includes a vacuum-controlled, tube-shaped resistor, having a fluid-flow passage, which is fixedly mounted in an aspiration line of the system to facilitate fluid flow therethrough. The resistor is composed of a material which will deform the fluid flow passage in response to an increase in negative pressure to reduce the cross-sectional area of the passage, and tends to reform to increase the flow area when the pressure of the aspiration line becomes less negative Thus, there is a need for a surgical apparatus which, when operating in an aspiration mode during a surgical procedure, will respond dynamically to changing fluid-flow conditions within fluid-flow passage of an aspiration line of the apparatus and facilitate dynamic adjustment of the size of the fluid-flow passage to sustain an established fluid-flow rate within the aspiration line.

There is a further need for a surgical apparatus which, when operating in an aspiration mode during a surgical procedure, will respond dynamically to a surge of fluid flowing within a fluid-flow passage of an aspiration line of the apparatus and dynamically restrict the size of the fluid-flow passage to establish a desired fluid-flow rate and quickly suppress the surge to prevent potential deleterious effects therefrom.

If a stubborn occlusion is encountered, which will not break free upon the application of the above-noted high level of vacuum pressure, the surgeon can initiate a reflux procedure by controlling the aspiration system to reverse the operation of the peristaltic aspiration pump, provided that the surgical apparatus is capable of operating in a reflux mode. During the reflux procedure, the fluid in the aspiration line will flow in a reflux direction, i.e., toward the site of the surgery, whereby the occlusion is forced, within the aspiration line, in a direction toward the site of the surgery, to break free from the occluding position. It is important that, during the reflux procedure, the aspiration line be unrestricted, to insure that the flow rate of the aspiration fluid, in the reflux direction, is sufficient to force the occlusion free.

If an attempt is made with the apparatus of the '271 patent to operate the apparatus in a reflux mode, the pre-set restrictive opening will preclude the aspiration line from being unrestricted, and will prevent the development of a force sufficient to break free the occlusion. Even if the restricted opening is as fully open as possible, the restriction imposed by the fully-open restrictive opening will not facilitate the development of the force necessary to break free the occlusion.

In the '560 publication, and the '367 and '620 patents, there is no showing of any facility for allowing unrestricted fluid flow in a reflux direction during a reflux mode.

Thus, there is a need for a surgical apparatus which, during an aspiration mode of operation of a surgical procedure, will respond dynamically to a surge of fluid flowing within a fluid-flow passage of an aspiration line of the apparatus and dynamically restrict the size of the fluid-flow passage to establish a desired fluid-flow rate which will quickly suppress the surge to prevent potential deleterious effects therefrom, and where the surgical apparatus will provide an unrestricted fluid-flow passage within the aspiration line of the apparatus during a reflux mode of operation with a force sufficient to break free any occlusion in the aspiration line.

SUMMARY OF THE INVENTION

It is, therefore, an object of this invention to provide a surgical apparatus which, when operating in an aspiration mode during a surgical procedure, will respond dynamically to changing fluid-flow conditions within a fluid-flow passage of an aspiration line of the apparatus and facilitate dynamic adjustment of the size of the fluid-flow passage to sustain an established fluid-flow rate within the aspiration line.

Another object of this invention is to provide a surgical apparatus which, when operating in an aspiration mode during a surgical procedure, will respond dynamically to a surge of fluid flowing within a fluid-flow passage of an aspiration line of the apparatus and dynamically restrict the size of the fluid-flow to establish a desired fluid-flow rate and quickly suppress the surge to prevent potential deleterious effects therefrom.

A further object of this invention is to provide a surgical apparatus which, during an aspiration mode of operation of a surgical procedure, will respond dynamically to a surge of aspirated fluid flowing within a fluid-flow passage of an aspiration line of the apparatus and dynamically restrict the size of the fluid-flow passage to establish a desired fluid-flow rate and quickly suppress the surge to prevent potential deleterious effects therefrom, and where the surgical apparatus will provide an unrestricted passage within the aspiration line of the apparatus during a reflux mode of operation.

Still another object of this invention is to provide a surgical apparatus which, during a surgical procedure, will minimize, if not eliminate, the negative effects of air existing within an aspiration line of the surgical apparatus, during the extraction of particles resulting from surgery at a site within a body cavity.

With these and other objects in mind, this invention contemplates a surgical apparatus having a dynamic surge suppressor which includes a dynamic surge suppressor for use in a phacoemulsification surgical procedure for the removal of lens tissue from an eye of a patient, which includes a suppressor housing having an inner passage and a mesh filter located within a portion of the inner passage of the suppressor housing. A tube, having an unobstructed inner passage with a prescribed diameter, is located in a portion of the inner passage of the suppressor housing not occupied by the mesh filter, and is unattached to any portion of the suppressor housing, and movable freely and independently within the inner passage of the suppressor housing. A separate inner passage, independent of the unobstructed inner passage of the tube, is formed by a space between an outer surface of the tube and an adjacent portion of an inner wall of the separate inner passage of the suppressor housing.

This invention also contemplates an in-line filter assembly for use in a phacoemulsification surgical procedure in the removal of lens tissue from an eye of a patient, which includes a filter housing having an input end with an opening, and formed with an inner passage extending, and having a uniform diameter, between the input end and an output end of the filter housing. A mesh filter is located within the inner passage of the filter housing and has an inlet opening located at an input end of the filter housing, and is uniformly spaced from an inner wall of the inner passage of the filter housing. An input luer, having a body which extends axially between an input end and an output end of the input luer, is formed with an input section and an output section. The input luer has a through passage which extends from the input end to the output end thereof, which includes an output passage section at the output end of the body having a uniform diameter. The output section of the input luer is located within the mesh filter at the open end of the mesh filter. A ratio of the uniform diameter of the inner passage of the filter housing to the uniform diameter of the output passage section of the input luer is less than two.

This invention further contemplates a method of dynamically altering a rate of flow of fluid through an aspiration line of an aspiration system used in a phacoemulsification procedure for the removal of lens tissue from an eye of a patient, and includes the steps of providing an aspiration line with a fluid flowing therethrough in an aspiration direction at a prescribed rate of flow; providing, in a section of the aspiration line, an unobstructed passage and a separate passage, arranged in a parallel and separate from each other; separating the fluid into two portions; moving a first portion of the two portions of fluid through the unobstructed passage; moving a second portion of the two portions of fluid through the separate passage; responding dynamically to a changed rate of flow from the prescribed rate of flow in the aspiration line; and adjusting dynamically a rate of flow of the second portion of the fluid through the separate passage to dynamically return the flow of fluid in the aspiration line to the prescribed rate of flow.

In addition, this invention contemplates a method of moving fluid through an aspiration line of an aspiration system in either an aspiration direction or a reflux direction during a phacoemulsification procedure for the removal of lens tissue from an eye of a patient, which includes the steps of providing an aspiration line with a fluid flowing therethrough in an aspiration direction at a prescribed rate of flow; providing, in a section of the aspiration line, a facility for adjusting the rate of flow of the fluid in the aspiration direction when a change occurs in the rate of flow from the prescribed rate of flow; and providing facility for reversing the direction of flow of the fluid in a reflux direction through the aspiration line.

Still further, this invention contemplates a method of filtering particles from a fluid flowing through an aspiration line of an aspiration system used in a phacoemulsification procedure for the removal of lens tissue from an eye of a patient, which includes the steps of providing a filter housing within an aspiration line of an aspiration system; mounting a filter within the filter housing such that a space is formed between an outer side surface of the filter and an inner side wall of the filter housing; moving particle-laden fluid into an inner passage of the filter and into the filter where the particles are captured in, and particle-free fluid moves through, the filter; and moving the particle-free fluid into the space between the filter and the filter housing, and out of the filter housing.

BRIEF DESCRIPTION OF THE DRAWINGS

Embodiments of the invention will now be described, by way of example only, with reference to the accompanying drawings, in which:

FIG. 9 is a sectional view showing a first modified portion of the dynamic surge suppressor of FIG. 7, which is a second practical embodiment thereof, in accordance with certain principles of the invention;

FIG. 10 is a sectional view showing a second modified portion of the dynamic surge suppressor of FIG. 7, which is a third practical embodiment thereof, in accordance with certain principles of the invention;

DETAILED DESCRIPTION OF THE PREFERRED EMBODIMENT

Figure 1:
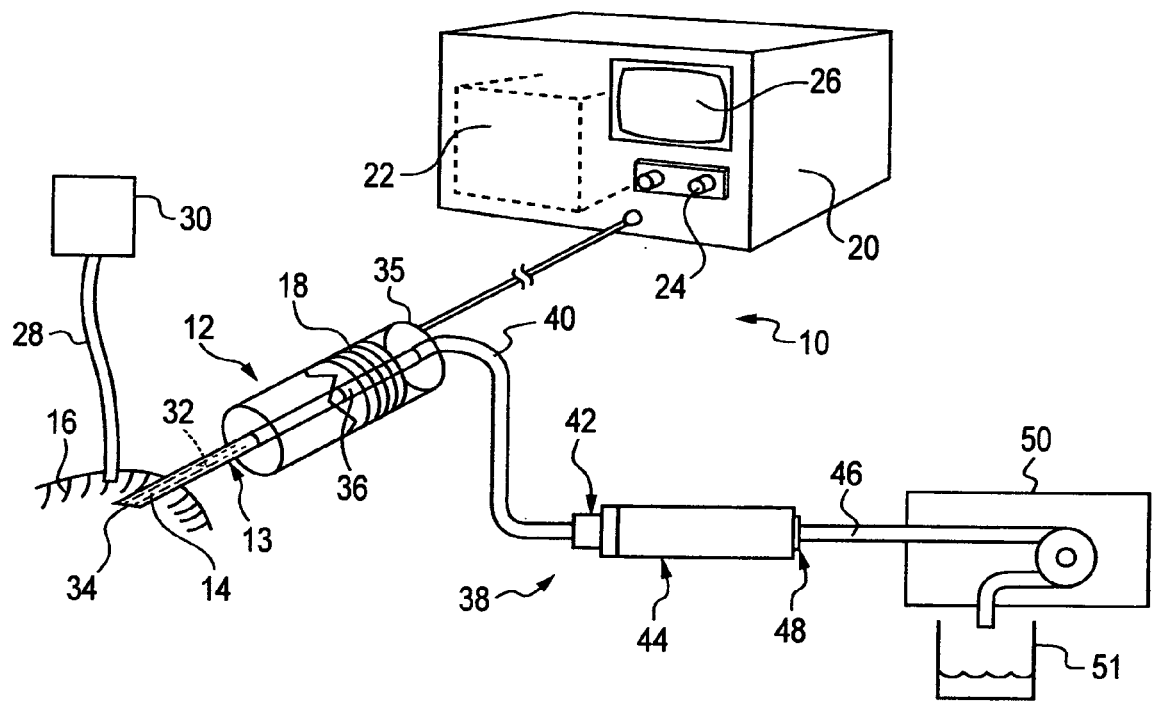
FIG. 1 is a schematic representation showing a surgical apparatus used in phacoemulsification procedure, in accordance with certain principles of the invention.

A surgical apparatus 10, as illustrated in FIG. 1, includes a hand piece 12, containing a needle-like, hollow cannula 13, which is formed with a free-end cannula tip 14 that extends from a forward end 15 of the hand piece. During a surgical procedure, the free-end tip 14 can be inserted into a cornea 16 of a patient's eye, through a small incision formed by the surgeon in the cornea. The hand piece 12 also contains one or more ultrasonic transducers 18 that convert electrical power into mechanical movement to ultrasonically drive the hollow cannula 13 and the tip 14. The hand piece 12 is typically held by a surgeon who performs the surgical procedure, such as, for example, a phacoemulsification procedure (hereinafter "the phaco procedure"), to break a lens, located within the cornea 16 and an anterior chamber of the eye, into particles and residual debris (hereinafter "the particles").

The hand piece 12 is connected to a console 20 of the surgical apparatus 10, which includes a control circuit 22 for providing driving signals to the transducers 18. The console 20 also has input knobs or buttons 24 that allow the surgeon to vary different parameters of the apparatus 10. Further, the console 20 has a readout display 26 that provides an indication of the power level, etc. of the apparatus 10.

The surgical apparatus 10 includes an irrigation tube 28 having a forward end located at the site of the surgical procedure, which is inserted into the cornea 16, and a rearward end, which is coupled to an irrigation source 30. The irrigation source 30 may be a gravity-feed bottle 30 that contains an irrigation fluid, such as, for example, a balanced salt solution, which flows from the irrigation source, through the irrigation tube 28, and is infused into the cornea 16 to facilitate removal or flushing of the particles from the patient's eye. A hollow passage of the irrigation tube forms an irrigation line, which facilitates flow of the irrigation fluid in an irrigation direction, i.e., from the bottle 30 towards the patient's eye. It is noted that the irrigation tube 28 may be coupled to the hand piece 12, where the directing of the irrigation fluid into the patient's eye may be controlled through manipulation of the hand piece by the surgeon during the surgical procedure.

The hollow cannula 13 is formed with a passage 32 therethrough, with an inlet opening 34 of the cannula located at the free-end tip 14 thereof. An inlet end of a luer 36 is connected to an outlet end of the cannula 13, and the luer extends rearward, and outward, from a rear end 35 of the hand piece 12, with an outlet end of the luer located outside of the cannula.

The surgical apparatus 10 further includes an aspiration system 38, with a filter assembly 44, which yields unexpected results in comparison with results yielded by prior disclosed aspiration systems (hereinafter "the prior disclosed system"). The aspiration system 38 aspirates the irrigation fluid and the particles out of, and away from, the patient's eye, in the form of an aspiration fluid and the particles.

An input end of a first aspiration tube, hereinafter referred to as "the input tube 40," having an inner passage 41, is connected to the outlet end of the luer 36, with an output end of the input tube 40 connected to an input end 54 of a cylindrically-shaped input luer 42, which forms a portion of a cylindrically-shaped in-line filter assembly 44, yielding unexpected results. A second aspiration tube, hereinafter referred to as "the output tube 46," has an input end connected to an output end of a cylindrically-shaped output luer 48 of the filter assembly 44, and an output end connected to a peristaltic pump 50. The peristaltic pump 50 is employed to pump the aspiration fluid, at a generally steady rate, from the patient's eye, and eventually into a fluid-collection chamber 51 at a site remote from the site of the surgery. Through the pumping action, the pump 50 also develops a low-level negative, or vacuum, pressure in the aspiration line, which, in conjunction with the pumped fluid flow, draws the fluid and particles from the patient's eye.

The aspiration system 38 includes the hollow cannula 13, the input tube 40, the input luer 42, the filter assembly 44, the output tube 46, and the pump 50, all hereinafter referred to as the components of the aspiration system. An aspiration line of the aspiration system 38 is formed by in-line, communicating, fluid-flow passages of the components of the aspiration system, beginning with the inlet opening 34 of the cannula 13 and terminating with the pump 50. As noted above, the peristaltic pump 50 facilitates the generally steady-rate flow of the aspiration fluid in an aspiration direction, i.e., from the patient's eye towards the pump, and the development of a relatively low-level vacuum pressure within the aspiration line. The steady-rate flow of the aspiration fluid, and the relatively low-level negative, or vacuum, pressure, are established by the surgeon through manipulation of the knobs 24 of the console 20. It is noted that the pumping action could be provided by a venturi pump or a diaphragm pump, but the peristaltic pump 50 is preferred.

The manner in which the peristaltic pump 50 develops fluid flow and vacuum pressure is described in a treatise titled, "PHACODYNAMICS Mastering the Tools and Techniques of Phacoemulsification Surgery," Second Edition, by Barry S. Seibel, MD, Copyright 1995 by SLACK Incorporated, ISBN 1-55642-256-3.

Figure 2:
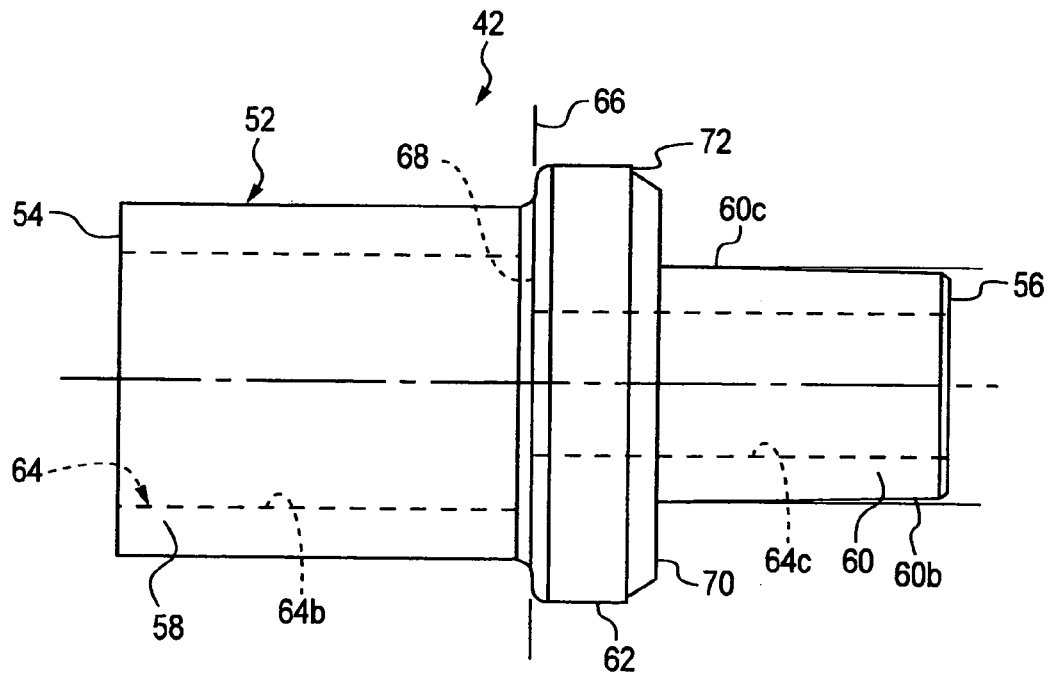
FIG. 2 is a side view showing an input luer of the surgical apparatus of FIG. 1, in accordance with certain principles of the invention.
Figure 3:
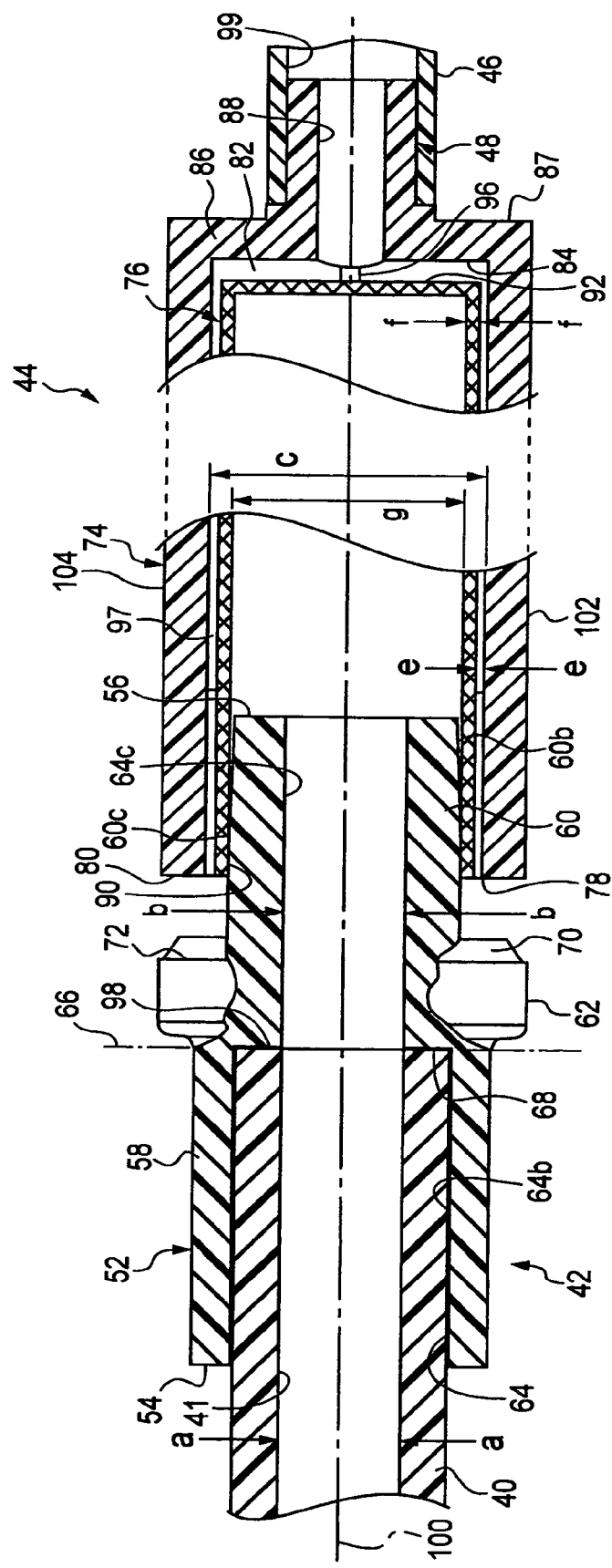
FIG. 3 is a sectional view showing the input luer of FIG. 2 in assembly with a filter housing, containing a filter, of the surgical apparatus of FIG. 1, in accordance with certain principles of the invention.

Referring to FIGS. 2 and 3, the input luer 42 is formed with a generally cylindrical body 52, which extends axially between the input end 54 and an output end 56 thereof. The body 52 includes an input section 58, an output section 60, and an intermediate, or flange, section 62 between the input section and the output section, all of which are axially aligned and integrally joined. The intermediate section 62 is formed with a largest external diameter, the output section 60 is formed with a smallest external diameter, and the input section 58 is formed with an intermediate external diameter, at a dimension between the dimensions of the largest diameter and the smallest diameter.

The exterior surface of the output section 60 of the input luer 42 is formed with a slight tapered portion 60b, which tapers outward, in an axial direction, from the output end 56 toward the intermediate section 62 of the input luer. The tapered portion 60b extends to an intermediate portion of the exterior surface of the output section 60, and joins with a non-tapered portion 60c of the exterior surface, which extends between the juncture of the non-tapered portion with the tapered portion and the intermediate section 62 of the input luer 42.

The input luer 42 is formed with a through passage 64, which extends from the input end 54 of the luer to the output end 56 thereof. The passage 64 is formed by a first passage section 64b, which extends from the input end 54 of the luer 42 to a transaxial plane 66, located at the juncture of the input section 58 and the intermediate section 62, and by a second passage section 64c, located between the transaxial plane and the output end 56 of the luer. The first passage section 64b is formed with a large diameter in comparison to a small diameter of the second passage section 64c, whereby a shoulder 68 is formed in the passage 64, coincidentally in the transaxial plane 66, where the passage transitions from the large diameter to the small diameter.

The body 52 of the input luer 42 is composed of a plastic material, and includes a structurally sacrificial extension 70, which extends from, and is integrally formed with, a rear face 72 of the intermediate section 62. The sacrificial extension 70 is formed with an energy director surface, which facilitates the ultimate ultrasonic welding of the input luer 42 with, and as an integral component of, the filter assembly 44 (FIGS. 1 and 3), as described below.

The filter assembly 44, as shown in FIG. 3, also includes a cylindrical filter housing 74, composed of a plastic material, and a cylindrical mesh filter 76 located within the housing. The housing 74 is formed with an opening 78 at an input end 80 of the housing, and with a cylinder-like inner passage 82, which extends, with a uniform inner diameter, from the input end of the housing to an inner surface 84 of a partial transaxial wall 86 at an output end 87 of the housing. The output luer 48 extends integrally and axially outward from the transaxial wall 86 of the housing 74, and has an inner passage 88, which is in communication with the inner passage 82 of the housing, and is formed with a diameter which is smaller than the uniform inner diameter of the inner passage of the housing.

The mesh filter 76 is exceptionally thin, with a thickness "f," and is cylindrical along an axis 100 thereof. As shown in FIG. 3, the filter 76 has an inlet opening 90, located at an inlet end of the filter. A closed mesh end 92 is formed at an output end of the filter 76. In this manner, the filter 76 assumes the structure of a pouch, or pocket, for receiving aspiration fluid and the particles therein, and allows passage of the fluid through the mesh of the filter. The aspirated particles are captured within the enclosure of the pouch of the filter 76, for eventual disposal with the filter assembly 44, following completion of the surgical procedure. The particle-free fluid exits through the inner passage 82 of the filter housing 74, the inner passage 88 of the outlet luer 48, and an inner passage 99 of the output tube 46, and is eventually deposited in the fluid-collection chamber 51.

In the preferred embodiment of the surgical apparatus 10, including the preferred embodiments of the aspiration system 38 and the filter assembly 44, the thickness "f" of the filter 76 is in a range between, and including, 0.005 inch and 0.010 inch, for reasons set forth below.

Figure 4:
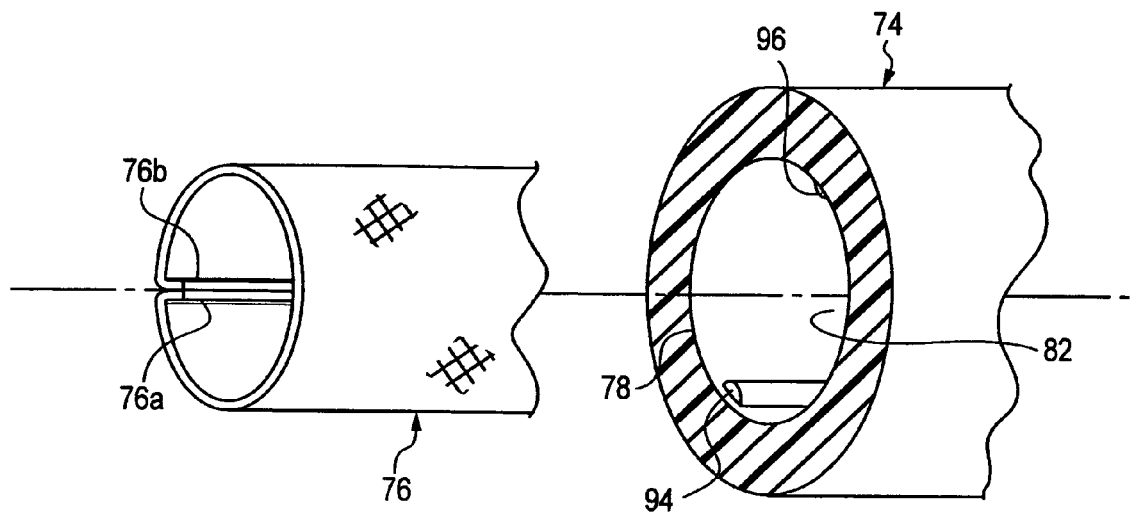
FIG. 4 is a perspective view showing portions of the filter and the filter housing of FIG. 3 in position for assembly, in accordance with certain principles of the invention.

As shown in FIG. 4, a pair of diametrically-spaced ribs 94 and 96 are formed on the wall of the inner passage 82 of the housing 74, and extend slightly radially into the inner passage, and longitudinally in an axial direction, from the inner surface 84 (FIG. 3) of the transaxial wall 86 (FIG. 3) of the housing toward the input end 80 of the housing, but not completely to the input end. When the filter 76 is placed through the opening 78 of, and eventually within, the inner passage 82 of the housing 74, longitudinal portions of the outer surface of the filter engage the radially inwardmost surface of each of the ribs 94 and 96, whereby the filter is maintained in its cylindrical configuration, and a space 97 (FIG. 3), having a radial distance "e," is formed between the outer surface of the filter and the wall of the inner passage 82. The radial distance "e" of the space 97 is determined by the radial dimensions of the ribs 94 and 96, the radial distance of which is also represented by the alpha-character "e" in FIG. 3, which is in a range between, and including, 0.005 inch and 0.015 inch.

In the preferred embodiment of the surgical apparatus 10, and the preferred embodiments of the aspiration system and the filter assembly 44, the radial distance "e" is in a range between, and including, 0.005 inch and 0.015 inch, and the axial length "l" of the inner passage 82 of the filter housing 74, between the inner wall 84 and the input end 80, is in a range between, and including, 1.150 inches and 1,250 inches, and each of the ribs 94 and 96 extend, in an axial direction, from the inner wall 84 towards the input end 80 but do not extend to a radial plane inclusive of the output end of the input luer 42, as shown in FIG. 3.

In the preferred embodiments of the aspiration system 38, and the filter assembly 44, the axial length "m" of the inner passage 82 of the filter housing 74, between the inner wall 84 and the input end 80, is in a range between, and including, 1.15 inches and 1.25 inches, and each of the ribs 94 and 96 extend from the inner wall 84 towards the input end 80 by a distance "o" in a range between, and including, 0.850 inch and 1.050 inches.

Referring again to FIG. 4, the filter 76 is initially formed into the cylindrical configuration by forming a flat sheet of mesh material, having opposite-side edges 76a and 76b, into a longitudinal cylindrical roll, and placing the longitudinal opposite-side edges radially inward of the roll, and in interfacing engagement. The interfacing engaged opposite-side edges 76a and 76b are thereafter secured to each other to maintain the formed filter 76 in the cylindrical configuration, with no portions of the filter extending outward from any portion of the outer surface of the filter. In this manner, subsequent to assembly of the filter 76 within the inner passage 82 of the housing 74, the outer surface of the filter is maintained in its cylindrical configuration, with all portions of the outer surface being separated from the adjacent portions of the inner wall of the housing by the radial dimension "e." With this arrangement, the outer surface of the filter 76 presents no impediments to the flow of fluid within the space 97 (FIG. 3).

Referring to FIG. 3, prior to assembling the input luer 42 with the housing 74, the closed mesh end 92 of the filter 76 is inserted into the inner passage 82 of the housing, and the closed end of the filter is moved to a position adjacent the inner surface 84 of the transaxial wall 86. Thereafter, the output section 60 of the input luer 42 is inserted into the inlet opening 90 of the filter 76, as illustrated in FIG. 3, and is moved farther into the inlet opening to a position where the sacrificial extension 70, with the energy-director surface, engages the input end 80 of the housing.

Figure 5:
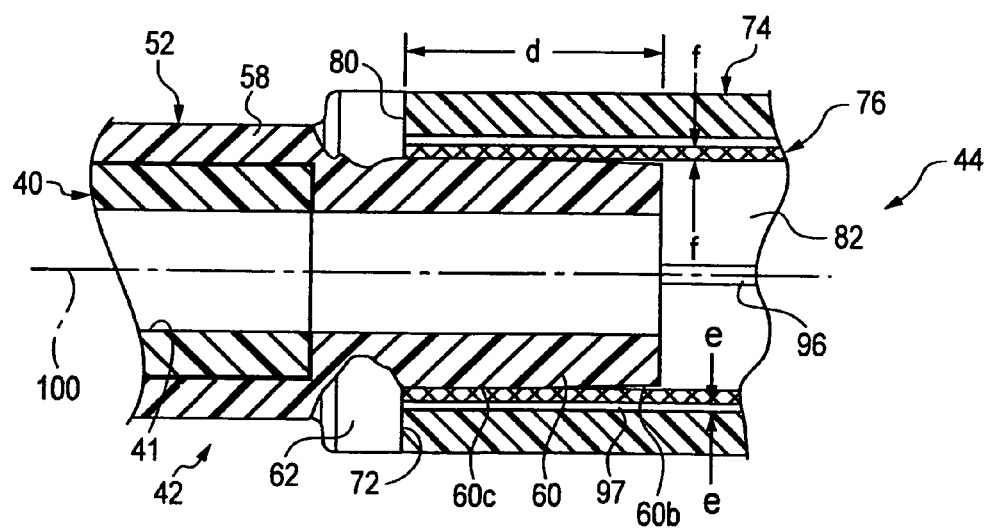
FIG. 5 is a sectional view showing portions of the input luer, the filter housing, and the filter, in accordance with certain principles of the invention.

Thereafter, during an ultrasonic welding process, the sacrificial extension 70 of the input luer 42 is transformed into a flowable state. With continued movement of the output section 60 into the filter 76, the rear face 72 of the intermediate section 62 of the input luer 42 is located adjacent the input end 80 of the housing 74. As illustrated in FIG. 5, upon curing of the flowable material of the sacrificial extension 70, and the adjacent portions of the rear face 72 of the input luer 42 and the input end 80 of the housing 74, the input luer and the housing are thereby welded together, to complete the filter assembly 44. The outlet section 60 of the input luer 42 is now located fully within an entry end portion of the filter 76, by an axial distance "d" from the opening 78 of the filter. It is noted that, subsequent to the welding process, the sacrificial extension 70 is no longer present in its original configuration, as shown in FIGS. 2 and 3, but has now blended with the adjacent portions of the rear face 72 and the input end 80 to form an air-tight seal and weld.

In the preferred embodiment of the surgical apparatus 10, and the preferred embodiments of the aspiration system 38 and the filter assembly 44, the axial distance "d" is in a range between, and including, 0.175 inch and 0.185 inch.

The tapered portion 60b of the output section 60 facilitates the insertion of the output section into the inlet opening 90 of the filter 76, and the inner portions of the filter, with relative ease. However, as the non-tapered portion 60c of the exterior surface of the output section 60, which trail the tapered portion 60b, are inserted into the inner portions of the filter 76, a substantial tight fit is formed between the interior of the filter and the non-tapered portion of the output section, which is sufficient to retain the filter in the assembled position with the output section 60.

In the preferred embodiment of the surgical apparatus 10, and the preferred embodiments of the aspiration system 38 and the filter assembly 44, the outer diameter of the non-tapered portion 60c, and the diameter of the interior of the filter 76, are each in a range between, and including, 0.110 inch and 0.115 inch, and are designated by the alpha-character "g" in FIG. 3.

It is noted that the inner diameter of the filter 76 could be slightly smaller than the outer diameter of the non-tapered portion 60c to enhance the tight fit arrangement, without departing from the spirit and scope of the invention.

An output end 98 of the input tube 40 is inserted into the first passage section 64b of the input luer 42, and is moved toward the shoulder 68 of the input luer until the output end 98 thereof abuts the shoulder of the input luer, whereby the input tube is now assembled with the filter assembly 44. An input end of the output tube 46 is moved over the output luer 48 to the position illustrated in FIG. 3, whereby the output tube is assembled with the filter assembly 44. An output end of the output tube 46 is coupled to the vacuum source 50, and the aspiration system 38 (FIG. 1) is now complete.

If the input tube 40 had been assembled about the outer surface of the input section 58 of the input luer 42, instead of within the first passage section 64b, the input end 54 of the input section would have presented an abutment to the incoming aspiration fluid, and the particles contained within the fluid, whereby some of the particles could have possibly been caught by the abutment. Since the velocity of the aspiration fluid through the aspiration line is quite high, i.e., approximately 2 meters per second, a bulk of the caught particles could be formed at the abutment, possibly resulting in the development of an occlusion, or partial occlusion, which could interfere with the desired operation of the aspiration system 38. By inserting the input tube 40 within the first passage section 64b, as is done in the preferred embodiment of the aspiration system 38, the undesirable accumulation of the particles at the abutment is avoided.

Also, if the input tube 40 had been assembled with the input luer in a manner which would have presented the abutment to the incoming aspiration fluid, a fluid turbulence would possibly have developed at the abutment, possibly resulting in the formation of air bubbles, and the deleterious effects thereof. With the input tube 40 being assembled within the input luer 42 in the manner described above, and illustrated in FIGS. 3 and 5, the fluid turbulence and the deleterious effects thereof are avoided.

Referring to FIG. 3, typically, when the aspiration system 38 is used as a component of the surgical apparatus 10 (FIG. 1) during a surgical procedure, the filter assembly 44 is placed in an alignment where the input luer 42 and the housing 74 are aligned about the centerline 100, in a horizontal orientation, with, for discussion purposes, a lower portion of the housing being referred to as a bottom 102 thereof, and an upper portion of the housing being referred to as a top 104 thereof.

With regard to the above-noted prior disclosed system, the flow of a fluid from a first conduit section of a flow path to a second conduit section of the flow path, the velocity in the aspiration direction, and the unimpeded flow, of the fluid is desirably sustained if the first section has an inner diameter which is smaller than the inner diameter of the second section. In this manner, there are no impediments to the flow of the fluid at the juncture of the first section with the second section. If the inner diameter of the first section is larger than the inner diameter of the second section, a shoulder, or abutment, is formed in the flow path of the fluid at a juncture of the first section with the second section, which presents an undesirable abutment to the velocity, and flow of at least some, of the fluid in the aspiration direction.

However, even where the inner diameter of the first section is smaller than the inner diameter of the second section, undesirable pockets of air, or air bubbles, are developed at the transition of the flow of the fluid from the first section to the second section. Ideally, then, to avoid the development of air bubbles, the inner diameter of the first section should be the same as the inner diameter of the second section. In some instances, this ideal structural arrangement is not practical for the intended functional purpose of the fluid flow system.

In order to minimize the above-noted undesirable development of air bubbles in the aspiration system 38, prior to the initiation of the above-noted phaco procedure, the in-line components of the fluid flow passage of the aspiration system, between, and including, the inlet opening of the cannula 13 and the outlet of the inner passage 82 of the housing 74, must be filled, or primed, quickly with fluid to a full level, and thereafter sustained at the rapid flow rate established by the peristaltic pump, to maintain the fluid at the full level during the phaco procedure. An innovative manner for effecting the purging process, where the filter assembly 44 is temporarily placed in a vertical orientation during the purging process, is described more fully below.

Experimentation has shown that the relative dimensions of the successively larger inner diameters, of the in-line components of the aspiration system 38, play a significant role in minimizing the development of air bubbles, during a phaco procedure. In the preferred embodiments of the surgical apparatus 10, and the preferred embodiments of the aspiration system 38 and the filter assembly 44, to achieve this structural goal of minimizing the development of air bubbles, the inner diameter of the hollow cannula 13 (FIG. 1), which is the smallest diameter of the fluid flow passage of the system, is 0.036 inch, and of the luer 36 (FIG. 1) is 0.070 inch, and, referring to FIG. 3, the inner diameter "a" of the inner passage 41 of the input tube 40 is in a range between, and including, 0.075 inch and 0.085 inch, the inner diameter "b" of the second passage section 64c of the input luer 42 is in a range between, and including, 0.105 inch and 0.120 inch, and the input diameter "c" of the housing 74 is in a range between, and including, 0.200 inch and 0.210 inch, for reasons set forth below.

During use of the above-noted prior disclosed system in a surgical procedure, an occlusion may occur at an inlet opening of a tip, which is the first component of the flow path of the prior disclosed system. The size of air bubbles, which are trapped within a filter-containing housing of the prior disclosed system, causes an undesirable increase in the accumulated vacuum energy within the system. When the occlusion eventually breaks free, an undesirable increase in the velocity of the fluid flow occurs. Ideally, this result could be avoided if the inner diameters of the housing and an immediately preceding fluid-input component of the flow path were the same. However, as noted above, this solution is not practical.

Experimentally, with respect to the aspiration system 38, it has been shown, unexpectedly, that the air bubbles inside the housing 74 can be reduced in size to acceptable levels when the input ratio of the inner diameter "c" of the housing to the inner diameter "b" of the second passage section 64c is less than two. With the size of the air bubbles in the housing 74 being at acceptable levels when the occlusion breaks free, the resulting fluid velocity is at an acceptable level, and the above-noted undesirable higher fluid velocity is avoided. For example, in the preferred embodiment of the surgical apparatus, and the preferred embodiments of the aspiration system 38 and the filter assembly 44, the inner diameter "c" of the housing 74 is in a range between, and including, 0.200 inch and 0.210 inch, and the inner diameter "b" of the second passage section 64c is in a range between, and includes, 0105 inch and 0.120 inch, whereby the input ratio is less than two. Other parameters for the inner diameters "b" and "c" could be chosen without departing from the spirit and scope of the invention, provided that the input ratio is less than two.

With reference to the prior disclosed system, when considering a theoretical condition in the above-noted prior disclosed system where no external bubbles exist in a limited portion of the fluid flow passage, exclusive of the inner passage of the filter-containing housing, the fluidic compliance of the limited portion is proportional to the volume of dissolved air in the limited portion, which, in turn, is proportional to the volume of fluid in the limited portion. However, when the volume of fluid in the inner passage of the housing is added to the volume of fluid in the limited portion, the fluidic compliance of the fluid flow passage of the conventional system is undesirably increased.

With respect to the aspiration system 38, it has been determined, unexpectedly, that to maintain the fluidic compliance at a desirable level, it is necessary to maintain the volume of the inner passage 82 of the housing 74 as small as possible, but large enough to (1) contain the filter 76, which has a volume sufficient to hold at least all of the aspirated particles of one cataract lens, and (2) provide for the space 97 between the outer surface of the filter and the wall of the inner passage, which is sufficient to facilitate continued flow of the filtered fluid through, and from within, the housing. With this design feature in mind, it has been determined that the filter 76 must have a volume which is less than two cc.

The above-noted prior disclosed system includes the housing, with a filter located axially within an inner passage of the housing, and arranged to provide a space between the filter and a wall of the inner passage of the housing, generally along the entire axial length of the filter. A fluid-delivery conduit includes portions which are located, for a predetermined axial distance, within an entry portion of an inner passage of the filter. In a particle-filtering process, particle-laden fluid is pumped by a fluid-flow pump, whereby the fluid flows from the fluid-delivery conduit, into the inner passage of the filter, through the filter where the particles are captured within the filter, into and through the space between the filter and the wall of the housing, and out of the housing.

During the particle-filtering process of the prior disclosed system, the housing is typically placed in a horizontal orientation, thereby defining a lower portion, or bottom, and an upper portion, or top, of the housing. As the particle-laden fluid flows through the flow path toward the housing, air bubbles develop within the moving fluid, and are carried into the housing. Theoretically, the vacuum draw would be sufficient to draw the air-containing fluid from the housing, through the filter and the above-noted space, and out of the housing. However, some of the air-containing fluid will locate within the portion of the filter and the space, which is adjacent the entry portion of the filter. In addition, air bubbles may migrate, and leak, through a juncture of the fluid-delivery conduit and the filter, and eventually into the space adjacent the entry portion of the filter.

In the prior disclosed system, while the fluid contained within the entry portion of the filter is withdrawn therefrom by the fluid pump and the pump-generated vacuum, any air bubbles contained within the entry portion of the filter tend to remain within the entry portion of the filter, and eventually migrate into the portion of the above-noted space adjacent the entry portion of the filter, between the filter and the wall of the inner passage of the housing. The pump is unable to withdraw the fluid and the migrated air bubbles contained within the fluid from within the space, whereby the fluid velocity at the inner wall of the housing, adjacent the entry opening of the filter, is zero. Under these conditions, the air bubbles, located within the portion of the space at the bottom of the horizontally-oriented housing, drift to the portion of the space at the top of the housing, and coalesce with air bubbles at the top to form larger air bubbles. Eventually, the larger air bubbles expand and occupy a major portion of the space adjacent the entry portion of the filter, and migrate into remaining portions of the space, which are not adjacent the entry portion of the filter. This causes the fluidic compliance to increase to unacceptable levels, and prevent the trapped air from being evacuated from the housing.

Therefore, it is extremely important that air bubbles developed in the housing be carried out of the housing with the fluid flowing through the housing.

When the aspiration system 38 is designed with tubing having typical dimensions, currently used in phaco aspiration systems, and with consideration of the parametrical requirements that (1) the above-noted input ratio be less than two, and (2) the above-noted filter volume be less than two cc, it has been determined that the inner diameter "c" of the inner passage 82 of the housing 74 must be in a range between, and including, 0.200 inch and 0.210 inch, in order to minimize the opportunity for air bubbles to drift to the top of the housing, and to prevent the air bubbles in the space 97 from coalescing into larger air bubbles.

By holding the radial distance "e" of the space, between the filter 76 and the wall of the inner passage 82 of the housing 74, to the range between, and including, 0.005 inch and 0.015 inch, this feature contributes to maintaining the diameter "c" in a range between, and including, 0.200 inch and 0.210 inch, and also provides the extremely limited space 97, which minimizes the opportunity for air bubbles to form, migrate, and coalesce into large air bubbles.

Each of the above-noted components of the aspiration system 38, and the filter assembly 44, contribute individually, and collectively, to the innovativeness of the preferred embodiments thereof. Other embodiments of the aspiration system 38, and the filter system 44, can be designed by following the requirements set forth above, without departing from the spirit and scope of the invention.

Figure 6:
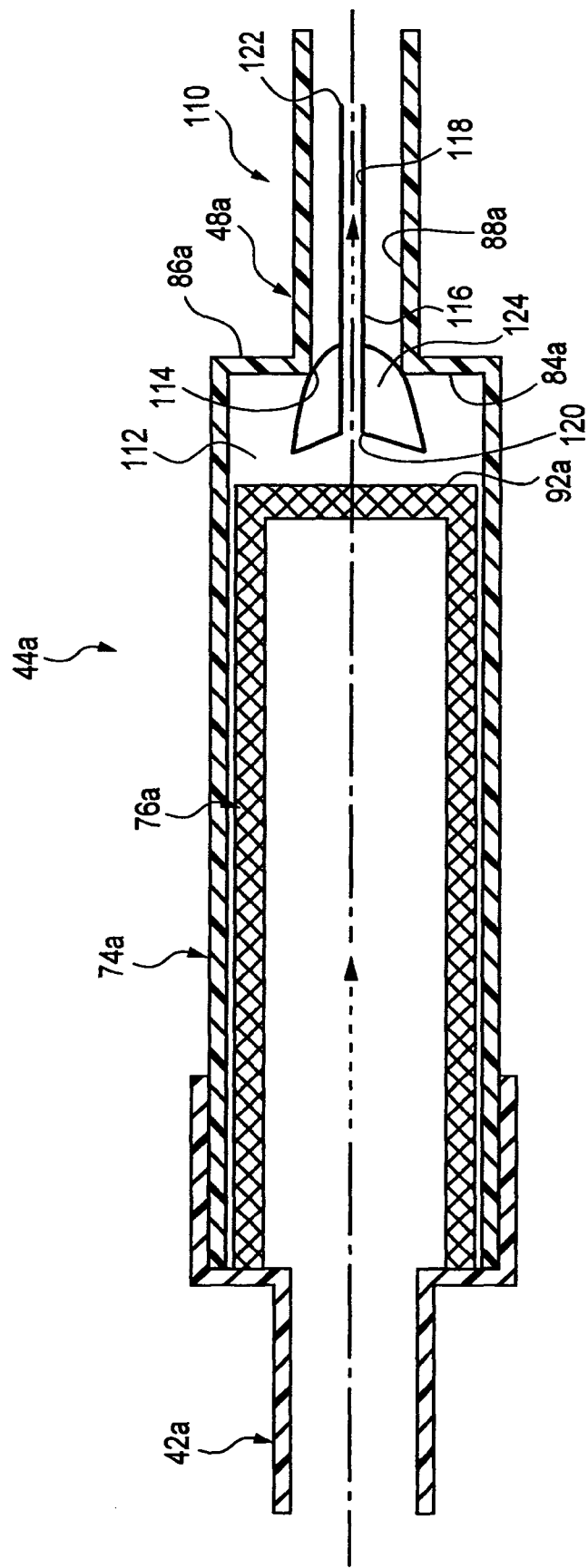
FIG. 6 is a schematic view showing a representation of an assembly of a dynamic surge suppressor of the surgical apparatus of FIG. 1, which includes structure similar to the input luer, the filter housing, and the filter, all of FIG. 5, and further includes a dynamic restrictor tube, all arranged in accordance with certain principles of the invention.
Figure 7:
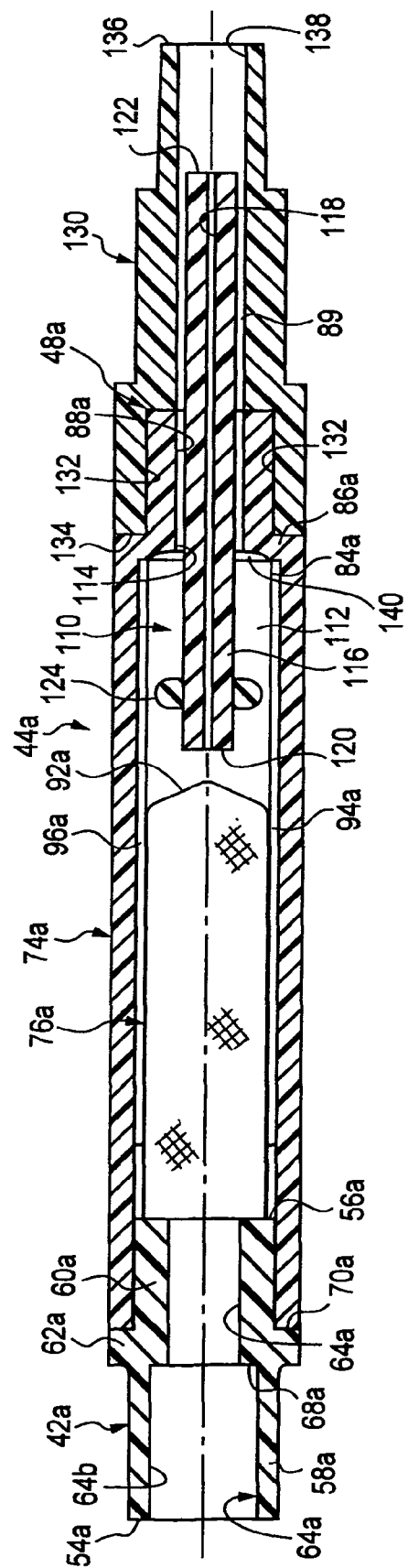
FIG. 7 is a sectional view of a first practical embodiment of an assembly of the dynamic surge suppressor of FIG. 6, in accordance with certain principles of the invention.
Figure 8:
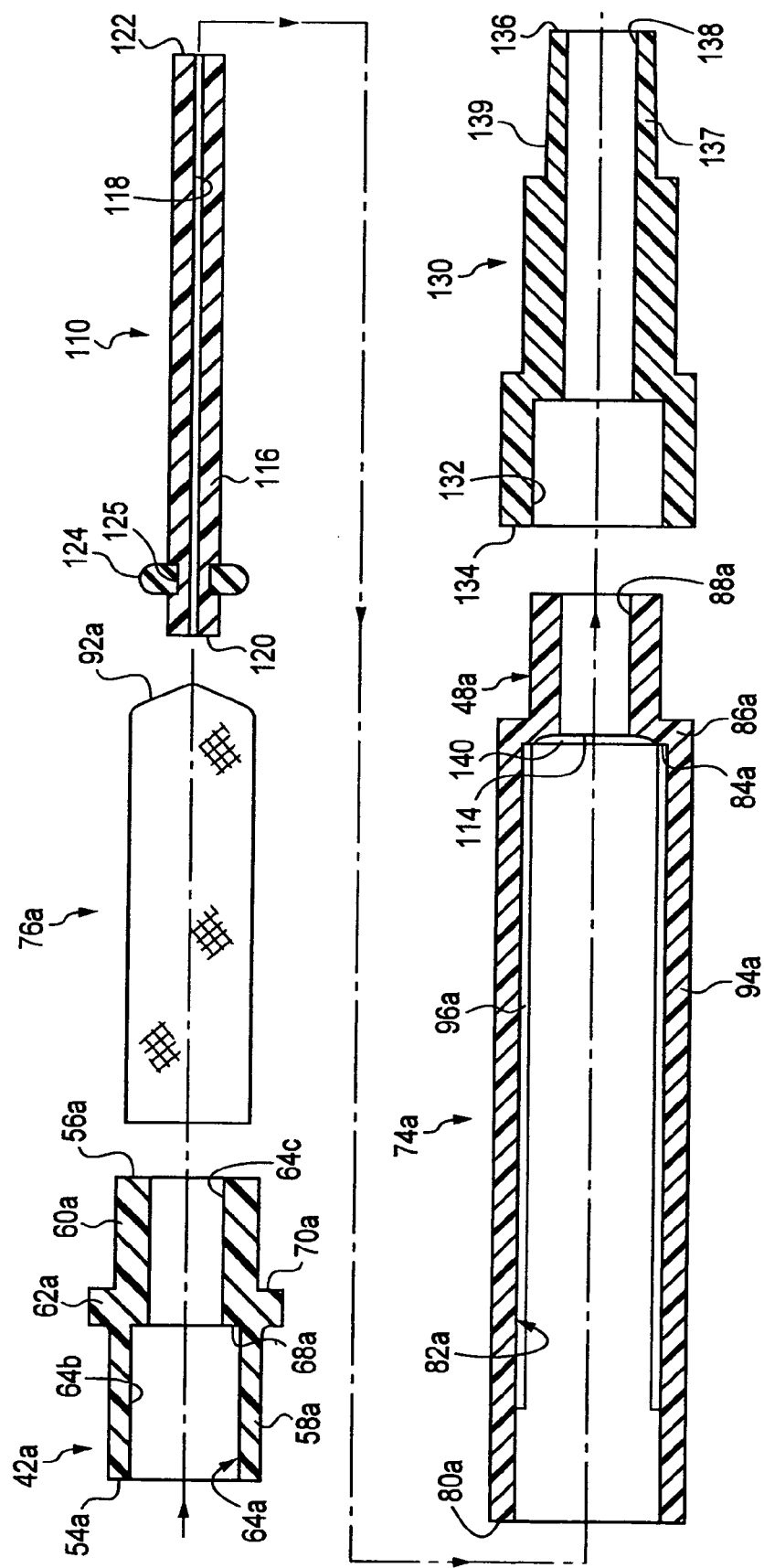
FIG. 8 is an exploded sectional view showing the components of the dynamic surge suppressor of FIG. 7 in spaced alignment to form the assembly, in accordance with certain principles of the invention.

The schematic illustration of FIG. 6, and the detailed illustrations of FIGS. 7 and 8, show a preferred embodiment of a dynamic surge suppressor 110 (hereinafter "the suppressor"), which forms a component of the preferred, and a first, embodiment of the surgical apparatus 10 of this invention. A first purpose of the suppressor 110 is to respond dynamically to undesirable variations in the flow rate of the aspiration fluid in the flow path, when the fluid is flowing in the aspiration direction, i.e., from the eye towards the peristaltic pump 50 as indicated by the dashed-line arrows in FIG. 6, and adjust, and maintain, the rate of flow to the desired steady rate of 50 cc/min or lower. A second purpose of the suppressor 110 is to respond dynamically to the surge of the aspiration fluid when an occlusion breaks free, and dynamically restrict the flow of the fluid through the flow path of the aspiration line to quickly decrease the flow rate to the desired 50 cc/min. A third purpose of the suppressor 110 is to facilitate an unrestricted flow of the fluid in the reflux direction, when the surgeon places the surgical apparatus 10 in the reflux mode.

In the following description regarding the suppressor 110, the structural configurations of many of the components of the surgical apparatus 10, as described below with respect to FIGS. 6 through 12, are essentially the same as corresponding components described above with respect to FIGS. 1 through 5. Where the components are essentially identical, the same numerical characters used above, in FIGS. 1 through 5, with respect to these components, will be used below, in FIGS. 6 through 12, with the addition of the alpha character "a." For example, the filter assembly 44, as described above, is essentially the same as the filter assembly described below, with respect to FIGS. 6 through 12, where the alpha/numerical character "44a" will be used to identify the filter assembly illustrated in FIGS. 6 through 12, and described below.

As illustrated in FIG. 3, the filter assembly 44 of the surgical apparatus 10 includes the filter housing 74, the filter 76 contained within the housing, and the input luer 42 ultrasonically welded to the input end 80 of the housing. The filter housing 74 is formed with the output luer 48 having the inner passage 88, which forms the fluid output of the housing. In the filter assembly 44, the closed mesh end 92 of the filter 76 is located in close proximity to the inner surface 84 of the transaxial wall 86 of the filter housing 74.

As illustrated in FIGS. 6, 7 and 8, the preferred embodiment of the surgical apparatus 10 includes a filter assembly 44a, with a filter housing 74a, a filter 76a, and an input luer 42a, which is essentially the same as the filter assembly 44, illustrated in FIG. 3, the exception being that a closed mesh end 92a of the filter 76a is spaced comparatively farther from an inner surface 84a of a transaxial wall 86a to form a chamber 112 between the closed mesh end of the filter and the inner surface of the transaxial wall. The filter housing 74a is formed with, or has ultrasonically welded thereto, an output luer 48a, which extends axially towards the peristaltic pump 50. The output luer 48a is formed with an inner passage 88a. An output port 114 is formed axially through the transaxial wall 86a, which provides fluid communication between the chamber 112 and the inner passage 88a of the output luer 48. The output port 114, in conjunction with adjacent portions of the inner passage 88a, forms a first portion of the aspiration line located in the vicinity of the output luer 48a, for fluid being moved through the aspiration line during the aspiration mode, as well as in the reflux direction during the reflux mode.

The suppressor 110 includes a cylindrically-shaped restrictor tube 116 formed with an axial, fluid-restrictive, inner passage 118, i.e., the unobstructed inner passage, extending axially through the tube, from an input end 120 to an output end 122 of the tube. It is noted that the inner passage 118 does not have any impediments to fluid flow, but is significantly restricted as to the volume of fluid, which is allowed to flow therethrough in a given period. A compliant member 124, such as, for example, a compliant O-ring, is positioned about an outer portion of the restrictor tube 116, near the input end 120 thereof, and is secured to the tube in that position. The compliant member 124 is preferably secured to the restrictor tube 116 by a tight friction-fit arrangement. Another technique for such assembly includes the formation of an annular groove 125 in the outer surface of the restriction tube 116, as shown in FIG. 8, which receives an inner annular surface portion of the compliant member 124 surrounding an axial opening thereof. In this instance, the annular groove 125 is formed with a diameter which is less than the remaining outside diameter of the restriction tube 116.

The preferred, and the first, embodiment of the surgical apparatus 10, which includes the preferred embodiment of the suppressor 110, is illustrated in FIGS. 6, 7 and 8, and is described, in part, above. In this preferred embodiment, the surgical apparatus 10 further includes a cylindrical luer-extender tube 130, which is formed with a cup-shaped opening 132 at an input end 134 thereof. The cup-shaped opening 132 fits snugly over the output luer 48a and is ultrasonically welded to the exterior of the transaxial wall 86a of the filter housing 74a. The luer-extender tube 130 extends to an output end 136 of an output section 137 of the tube, having a tapered external surface 139, and is formed with an inner passage 138, which is axially aligned with, and is formed with the same diameter as, the inner passage 88a of the output luer 48a. With this arrangement, the restrictor tube 116 is confined along its entire length within the chamber 112 and the axially aligned inner passages 88a and 138. However, the suppressor 110 is not physically connected or coupled to any portion of the surgical apparatus 10, and is thereby allowed to move, or "float," within the chamber 112 and the aligned inner passages 88a and 138 independently of any other portions of the surgical apparatus. The inner passages 88a and 138 also combine to form a rigid protective enclosure for those portions of the restrictor tube 116 which travel outside the chamber 112 during a phaco procedure.

A concave recess 140 is formed in the inner surface 84a of the transaxial wall 86a, and about the output port 114 of the filter housing 74a. The concavity of the recess 140 is formed generally in the cross-sectional shape of an interfacing side of the compliant member 124 to provide a sealing pocket for the compliant member as the compliant member is moved into the pocket to block or seal the output port 114.

It is noted that a suppressor housing is formed by the combination of the filter housing 74a and the luer extender 130, with the filter housing being referred to as a filter-housing portion of the suppressor housing. The suppressor housing has an inner passage formed by the inner passage 82a, the chamber 112, the output port 114, and the inner passage 88a, all of the filter housing, the inner passage 138 of the luer extender 130, and the inner passage 118 of the restrictor tube 116.

It is noted further that the compliant member 124 functions as a force responder, which responds to the force of fluid flowing in the inner passage of the suppressor housing, in either direction, for facilitating axial movement of the tube in either axial direction. The compliant member 124 also functions as a limiter, which, under the force of fluid flowing in the inner passage of the suppressor housing, engages structure, such as, for example, the transaxial wall 86a of the filter housing 74a, to limit the axial movement of the tube 116.

A second embodiment of the surgical apparatus 10 is shown in FIG. 9, wherein a luer extender 130a is formed integrally with the filter housing 74a, instead of as a separate component such as the luer extender tube 130, shown in FIG. 8. Functionally, the second embodiment of the surgical apparatus 10 operates in the same manner as the first embodiment thereof, as illustrated in FIG. 8.

A third embodiment of the surgical apparatus 10 is shown in FIG. 10, and includes a chamber tube 150, which is formed with a deep bore 152 from an input end 154 thereof. The tube 150 is formed with an axial inner passage 156 which extends from a base 158 of the bore 152 to an output end 160 of the tube. A portion of the bore 152, at the input end 154, is positioned over the output luer 48a of the filter housing 74a, and the input end 154 is ultrasonically welded to the exterior of the transaxial wall 86a of the housing. The axial length of the output luer 48a is less than the axial length of the bore 152, whereby a chamber 112a is formed in the portion of the bore not occupied by the output luer 48a. The suppressor 110 is assembled within the chamber 112a and the inner passage 156, with the compliant member 124 being located in the chamber. The base 158 of the bore 152 is formed with an inlet opening 114a, and a concave recess 140a about the inlet opening.

The third embodiment of the surgical apparatus 10 operates in a manner similar to the first and second embodiments thereof, except that the chamber 112a is not contained within the inner passage 82a of the filter housing 74a compared to the chamber 112, of the first and second embodiments, being located in the inner passage 82a.

As noted above, the surgeon uses the surgical apparatus 10 to conduct a phaco procedure for the removal of a cataractous lens of the patient. Prior to the surgery, the surgeon conducts the above-noted purging process within the aspiration system 38 to insure that any air bubbles which would normally develop in the aspiration line, during the initial feeding of the aspiration fluid into the line, is reduced or, preferably, prevented.

In preparation for the purging process, the filter assembly 44a is placed in a vertical orientation, rather than the typical phaco-operational horizontal orientation. With the filter assembly 44a arranged in the vertical orientation, the input luer 42a is located at the lower end, or bottom, of the vertically-oriented filter assembly, and the output luer 48a is located at the upper end, or top, of the vertically-oriented filter assembly. The purging fluid is then fed into the input end 34 of the cannula 13, through the aspiration line, and eventually into the fluid-collection chamber 51. With the purging fluid passing through the vertically-oriented filter assembly 44a, from the lower end of the filter assembly to, and through, the upper end of the filter assembly, the opportunity for the development of air bubbles during the purging process is significantly less likely than if the purging process was being conducted with the filter assembly being in any orientation other than the vertical orientation. Following completion of the purging process, i.e., when the aspiration line is completely filled with fluid, and in preparation for the phaco procedure, the filter assembly 44a can be repositioned to any other orientation, preferably a horizontal orientation.

The surgeon also initiates, and sets, the operation of the peristaltic pump 50 to operate at a desired steady flow rate of the particle-containing aspiration fluid, to move the fluid away from the patient's eye. The preferred flow rate in the surgical apparatus 10, of this invention, is 50 cc/min, but could be at any desired level within a range of 10 cc/min through 50 cc/min. Also, the surgeon sets the vacuum pressure within the aspiration line to a level within a range of 20 mmHg through 50 mmHg, with the preferred level, of this invention, being 50 mmHg.

The above-noted infused irrigation fluid is typically introduced into the eye at a flow rate of 70 cc/min. Due to the small size of the incision, and with the flow rate of the aspiration fluid set at 50 cc/min as noted above, a balance is created between the flow rates of the irrigation fluid and the aspiration fluid, which insures that there is always fluid in the eye, during an unoccluded operation, and that there is no excessive fluid-withdrawal rate of flow that could cause deleterious movement and/or collapse of the eye. As noted above, the vacuum pressure is developed by the pumping action of the peristaltic pump 50.

During the phaco procedure, the surgeon uses the free-end tip 14 of the hollow ultrasonically-driven cannula 13 to separate the lens into several parts such as, for example, four parts. Thereafter, the surgeon manipulates the hand piece 12, and the ultrasonically-driven cannula 13, to break each of the four parts of the lens into the particles, which migrate into the irrigation fluid within the anterior chamber of the eye. The peristaltic pump 50 facilitates the above-noted steady withdrawal rate of 50 cc/min of the aspiration fluid and the particles. To sustain a free flow, i.e., no occlusions, of the particle-laden aspiration fluid, a small amount of vacuum needs to be generated in the aspiration line. As noted above, this is accomplished by the peristaltic pump 50, which is set at the pressure level of 50 mmHg. The generated vacuum pressure assists in drawing the various-sized particles, with the fluid, away from the eye to facilitate the maintenance of the steady rate of flow of the aspiration fluid and the particles through the aspiration line. The particle-laden fluid is thereby pumped into the filter 76, where the particles are collected within the filter, and the particle-free fluid is pumped to, and deposited in, the fluid-collection chamber 51.

The surgical apparatus 10 will continue to function in the manner described above, provided that there are no occlusions in the aspiration line, which would cause the fluid to cease flowing. An occlusion could result from the presence of a large particle, which is of sufficient size to block the inlet opening 34 of the cannula 13. Such occlusions may also be formed by a collection of particles, and may be formed in, and block, other portions of the aspiration line.

When an occlusion occurs in the aspiration line, the flow path for the flow of the aspiration fluid is blocked, and the fluid ceases to flow as noted above. In such instances, the occlusion must be removed quickly and the aspiration system 38 returned to normal operation to avoid causing potentially critical disruption in the phaco procedure and potential deleterious movement, or collapse, of the eye.

During the period of an occlusion, the peristaltic pump 50 remains operational in the aspiration system 38, whereby the vacuum pressure rises significantly in the aspiration line, reaching pressure levels of 200 mmHg, and could approach 400 mmHg to 500 mmHg, in order to break free the occlusion. Where a typical size tubing and cannula 13 are used in the surgical apparatus 10, when the occlusion eventually breaks free, the high vacuum pressure, present in the aspiration line, causes a sudden surge in the flow rate of the now-pumped aspiration fluid within the aspiration line, frequently exceeding a surge rate of 200 cc/min. Due to the small size of the incision in the patient's cornea 16, the infusion flow rate of the irrigation fluid cannot exceed 70 cc/min The high surge rate of the fluid flow in the aspiration line creates a significant and undesirable imbalance with respect to the flow rates of the infused irrigation fluid and the surging aspiration fluid. This imbalance condition must be addressed promptly in order to prevent dislocation of elements of the eye, and, perhaps, the collapse of the eye.

Also, during the normal flow of the particle-laden fluid through the aspiration line generally at the flow rate of 50 cc/min, some particles, which are too small to cause an occlusion, may be of sufficient size, individually or collectively, to introduce a tendency toward a lowering of the desired steady rate of flow of the fluid within the aspiration line, thereby causing an undesirable sluggish operation.

As shown in FIG. 7, the compliant member 124 is captured within the chamber 112, but is allowed to move axially within the chamber, between prescribed limits defined by the closed mesh end 92a of the filter 76a, which is engagable with the input end 120 of the restrictor tube 116, and the output port 114 of the filter housing 74a, which is engagable with the compliant member 124. Due to the securing of the compliant member 124 with the restrictor tube 116, axial movement of the restrictor tube is limited to the allowable axial movement of the compliant member within the chamber 112 between the above-noted prescribed limits. Otherwise, as noted above, the surge suppressor 110, formed by the restrictor tube 116 and the compliant member 124, is not secured to any structure, and is allowed to "float" freely between the prescribed limits.

At different periods of the operation of the surgical apparatus 10 in the aspiration mode, and in the reflux mode, portions of the restrictor tube 116 will be located within corresponding portions of the inner passage 88a of the output luer 48a, and the inner passage 138 of the luer extender 130 with the remainder portions of the restrictor tube, and the entirety of the compliant member 124, being located in the chamber 112. With portions of the restrictor tube 116 being located within the inner passage 88a of the output luer 48a, and the inner passage 138 of the luer extender 130, a fluid-flow passage 89, i.e., a separate inner passage, separate from the inner passage 118 of the restrictor tube 116, is formed between any portion of the outer surface of the restrictor tube and the adjacent inner surfaces of the inner passages 88a and 138. The fluid-flow passage 89 is referred to as the separate inner passage, i.e., separate from the inner passage 118 of the restrictor tube 116.

In this manner, the inner passage 118 of the restrictor tube 116 forms a first channel of the aspiration line in the vicinity of the output luer 48a, for the uninterrupted, but restricted, flow of fluid being moved through the aspiration line during the aspiration mode, as well as in the reflux direction during the reflux mode. Also, the output port 114 and the passage 89 form a second channel of the aspiration line in the vicinity of the output luer 48a, for fluid being moved through the aspiration line during the aspiration mode, as well as for unrestricted fluid flow in the reflux direction during the reflux mode.

The inner passage 118 of the restrictor tube 116 is formed with a fixed diameter completely through the tube from, and through, the input end 120 to, and through, the output end 122 of the tube. The "floating" restrictor tube 116 is generally axially movable within the fluid flowing through the chamber 112 and the fluid flowing through the output port 114 and the passage 89, but only within the above-noted prescribed limits imposed upon axial movement of the suppressor 110 in the chamber 112. Thus, in the preferred embodiment of the invention, the output port 114 of the filter housing 74a and the passage 89, and the inner passage 118 of the restrictor tube 116, provide parallel paths for fluid flow through the aspiration line, in the vicinity of the output luer 48a during operation in the aspiration moce and the reflux mode. It is noted that the paths for fluid flow, including the output port 114 and the passage 89, and the inner passage 118, could be arranged in an orientation other than parallel without departing from the spirit and scope of the invention During use of the surgical apparatus 10, including the suppressor 110, while operating in the aspiration mode, particle-laden aspiration fluid enters the filter assembly 44a through the input luer 42a, and flows into the filter housing 74a at the steady rate of 50 cc/min, as established by the peristaltic pump 50. As the particle-laden fluid flows through the filter 76a, the particles are filtered out of the fluid and are captured within the filter. The particle-free fluid then flows from the filter 76a, and into the chamber 112. Thereafter, a first portion of the particle-free fluid will flow through the first channel, formed by the restrictive inner passage 118 of the restrictor tube 116, and, assuming that the output port 114 is not blocked by the compliant member 124, a second portion of the particle-free fluid will simultaneously flow through the second channel formed by the output port and the passage 89. The first and second portions of the flowing fluid will rejoin at the outlet end 122 of the restrictor tube 116, and continue through the portion of the inner passage 138 of the luer extender 130, and will eventually be deposited in the fluid-collection chamber 51.

The compliant member 124, as shown in FIG. 6, is in a blocking position to block or seal the output port 114 of the filter housing 74a to preclude the flow of fluid from the chamber 112 into, and through the second channel, i.e., the output port 114 and the passage 89. Under certain fluid-flow conditions as described below, movement of the compliant member 124 into the blocking position, about the output port 114, is accomplished when the forces of the aspiration fluid moving in the aspiration direction, as provided by the pumping action of the peristaltic pump 50, are sufficient to effect such blocking movement such as, for example, upon the occurrence of above-noted fluid surge following the removal of an occlusion.

Referring to FIG. 7, when such above-noted forces are insufficient to move the compliant member 124 into the blocking position, the compliant member assumes one of a plurality of axial non-blocking positions within the chamber 112, where such non-blocking positions are spaced, by successive distances, from the output port 114 of the housing 74a towards the closed mesh end 92a of the filter 76a. When the compliant member 124 is located in any of the non-blocking positions, fluid is allowed to flow, during the aspiration mode and in an aspiration direction, from the chamber 112, through the second channel formed by the output port 114 and the passage 89, and into, and through, the inner passage 138 of the luer extender 130.

However, placement of the compliant member 124 in successive non-blocking positions, which are successively closer to the output port 114, partially restricts the output port by corresponding successively increasing amounts to gradually restrict the flow of fluid from the chamber 112 and through the second channel formed by the output port and the passage 89, and into the inner passage 138 of the luer extender 130. Placement of the compliant member 124 in successive non-blocking positions, which are successively farther from the output port 114, gradually lessens the restriction of the flow of fluid through the output port, so that the fluid moves more freely from the chamber 112 and through the second channel formed by the output port and the passage 89.

During periods when there are no occlusions blocking the aspiration line, the forces of the pumping action of the peristaltic pump 50, at the flow rate of 50 cc/min, and the vacuum pressure, at 50 mmHg, are insufficient to move the compliant member 124 into the blocking position about the outlet port 114, whereby the compliant member assumes one of the plurality of non-blocking positions. Under this operating condition, the fluid is allowed to flow through the second channel formed by the outlet port 114 and the passage 89, and through the restrictive first channel formed by the inner passage 118 of the restrictor tube 116, and into the inner passage 138 of the luer extender 130.

Since the compliant member 124 is secured to the outer portion of the restrictor tube 116, and is thereby not blocking the input end 120 or the output end 122 of the restrictor tube, fluid will be allowed to flow unimpeded, but restricted, through the first channel, i.e., the inner passage 118 of the restrictor tube, at any time when the fluid is flowing in the aspiration line, in either the aspiration mode or the reflux mode. Therefore, fluid flowing into the chamber 112 from the filter 76a, in the aspiration mode, will flow through the inner passage 118 of the restrictor tube 116 in an unimpeded but restrictive manner, and into the inner passage 138 of the luer extender 130. In the reflux mode, fluid will flow unimpeded, in the reflux direction, into the output end 122 of the restrictor tube 116, through the first channel formed by the inner passage 118, out of the input end 120, and into the chamber 112. As fluid flows into the chamber 112 in the reflux direction, through the first channel and the second channel, the force of the incoming fluid will urge the compliant member 124 to its farthest possible position from the outlet port 114, thereby opening the second channel as fully as possible allowing for maximum unrestricted flow of fluids during a reflex mode.

During unoccluded operation of the surgical apparatus 10, particle-free fluid is flowing from the filter 76a into the chamber 112 at the established rate of 50 cc/min, and the compliant member 124 is located at one of the non-blocking positions located in the chamber 112, which is spaced from the output port 114 toward the filter 76a. As noted above, the forces of the fluid flowing at the rate of 50 cc/min, and the vacuum pressure, as applied against the compliant member 124, determine the precise non-blocking position at which the compliant member is located at this stage of the phaco procedure. The location of the precise non-blocking position, representative of the desired flow rate of 50 cc/min, is established when the peristaltic pump 50 is initially set to provide the desired steady flow rate and the desired vacuum pressure. This location of the compliant member 124 establishes a prescribed restriction, but not blockage, to the flow of the fluid to, and through, the output port 114 representative of the establishment of the steady flow rate of 50 cc/min.

Large particles in the pre-filtered fluid, which are not sufficient to create an occlusion, tend to create a drag on the flow of the fluid, whereby the flow rate of the fluid drops below the established rate of 50 cc/min. While this drop in the flow rate is not critical to the phaco procedure, it does create a less than desirable condition, which should be addressed to maintain consistency in the phaco procedure.

As the flow rate drops below 50 cc/min during an aspiration procedure, the suppressor 110 dynamically, and immediately, responds by initiating a process for returning the lowered flow rate to 50 cc/min. During this process, the lowered flow rate causes a lowering of the above-noted forces applied to the compliant member 124, whereby the compliant member, with the restrictive tube 116, moves to another non-blocking position, in the chamber 112, farther from the output port 114, thereby lessening the above-noted prescribed restriction, imposed by the compliant member, in the path of the fluid flowing from the chamber towards, and through, the output port. As the compliant member 124 is moved farther from the output port 114, and the restriction to fluid flow into, and through, the output port is lessened, the fluid moves more freely through the output port into the passage 89, resulting in an increase in the now-lower flow rate of the fluid. As the fluid flow rate increases, the above-noted forces applied against the compliant member 124 increase to move the compliant member closer to the output port, and to the precise non-blocking position to re-establish the flow rate to 50 cc/min.

During the phaco procedure, the suppressor 110 is continuously monitoring the flow rate of the aspiration fluid, and dynamically responds, in the manner noted above, to correct deviations in the desired flow rate of 50 cc/min, and, thereby, moves to and fro, or oscillates, relative to the output port 114 to maintain the desired flow rate. It is noted that, during this period of varying restriction of the fluid flowing towards, and through, the output port 114, the fluid continues to flow, unimpeded, through the inner passage 118 of the restrictor tube 116.

When an occlusion occurs in the aspiration line, the fluid flow path is blocked and the fluid ceases to flow, whereby the compliant member 124, with the restrictor tube 116, floats freely within the chamber 112 away from the output port 114, allowing the vacuum pressure to increase in the aspiration line, due to the continuation of the operation of the peristaltic pump 50. The vacuum pressure continues to be applied to the aspiration line, as noted above, with the pressure increasing significantly toward 200 mmHg, and perhaps as high as 400 mmHg to 500 mmHg, to provide sufficient suction to draw the occlusion into the flow path of the fluid, in the aspiration direction. When the occlusion breaks free, and is drawn into the aspiration line under the significantly high vacuum pressure, the fluid flow returns. However, due to the presence of the above-noted high vacuum pressure in the aspiration line at the instant the occlusion breaks free, the fluid surges in the aspiration direction to a significantly high flow rate such as, for example, 200 cc/min. As noted above, this high-rate surge creates an imbalance between the infused irrigation-fluid flow rate of 70 cc/min and the surging aspiration flow rate, which could have deleterious results regarding the health of the patient's eye. This situation must be addressed quickly.

When the occlusion breaks free, and the fluid surges to the high flow rate, the force of the surging fluid, in the aspiration direction, the suppressor 110 dynamicly and quickly responds whereby the compliant member 124 is quickly urged toward, and blocks or seals, the output port 114 to preclude the flow of any fluid through the output port and into the passage 89. With the output port 114 being blocked, the only flow path for the surging fluid is through the unimpeded inner passage 118 of the restrictor tube 116. The size, or diameter, of the inner passage 118 is extremely small, as noted below, and, coupled with the length of the restrictor tube 116, i.e., the length of the extremely small restrictive inner passage 118, the volume of fluid allowed to flow through the inner passage is significantly restricted. Due to the flow-rate restriction imposed by the small size, and length, of the inner passage 118, the rate of the surging fluid, which is precluded from flowing through the blocked output port 114, is quickly lowered to a level approaching the desired flow rate of 50 cc/min.

As the flow rate approaches the desired flow rate, the force of the aspiration fluid in the aspiration direction is insufficient to retain the compliant member 124 in the position of blocking the output port 114, whereby the compliant member moves away from the output port to allow the fluid to again flow through the second channel, i.e., the output port and the passage 89. As the rate of flow reaches the desired rate of 50 cc/min, the compliant member 124 is now located at the precise non-blocking position to maintain the desired fluid flow rate as described above.

In the manner described above, the suppressor 110 dynamically responds to the changing conditions in the aspiration line created by a slowing flow rate, and a breaking free of an occlusion, to maintain real-time dynamic control of the operation of the surgical apparatus 10 during a phaco procedure. This allows the surgeon to perform the phaco procedure with minimal concern for certain undesirable changing conditions of the type encountered in the past while conducting the procedure.

If a stubborn occlusion is encountered during the phaco procedure, which cannot be removed by the increased vacuum pressure as noted above, the surgeon may initiate the reflux procedure by reversing the driving direction of the peristaltic pump 50, whereby the fluid will flow through the aspiration line, but in the reflux direction, i.e., in a direction from the peristaltic pump towards the eye of the patient. In the reflux mode, the fluid will enter the output end 136 of the luer extender 130, and flow into and through the second channel, i.e., through the passage 89, through the output port 114, and into the chamber 112. As the fluid flows into the chamber 112, the force of the flowing fluid urges the compliant member 124 considerably away from the output port, and farther into the chamber 112, whereby the fluid is allowed to move unimpeded in the reflux direction. Also, during the reflux mode, the fluid will flow in the reflux direction, unimpeded, through the restrictive inner passage 118 of the restrictor tube 116, and into the chamber 112. Eventually, the fluid flowing in the reflux direction will force the stubborn occlusion free of its blocking position, and thereby open the aspiration line. The surgeon then resets the peristaltic pump 50 to move the fluid in the aspiration direction, and the surgical apparatus 10 is thereby returned to the aspiration mode and operates in the manner described above.

During the above-described operation of the suppressor 110 in the aspiration mode, the suppressor is considered to be means, responsive dynamically to a change in fluid flow rate from a prescribed flow rate, for dynamically adjusting the flow rate to return to the prescribed flow rate. Further, the suppressor 110 is considered to be means, responsive dynamically to a surging flow rate of aspiration fluid at a level higher than a prescribed flow rate, for dynamically lowering the surging flow rate to a level approaching the prescribed flow rate. Also, the suppressor 110 is considered to be means, responsive dynamically to changing flow conditions of a fluid flowing in a first direction, for dynamically restricting the flow in the first direction, and means for facilitating unrestricted flow of a fluid in a second direction, different from the first direction.

Figure 11:
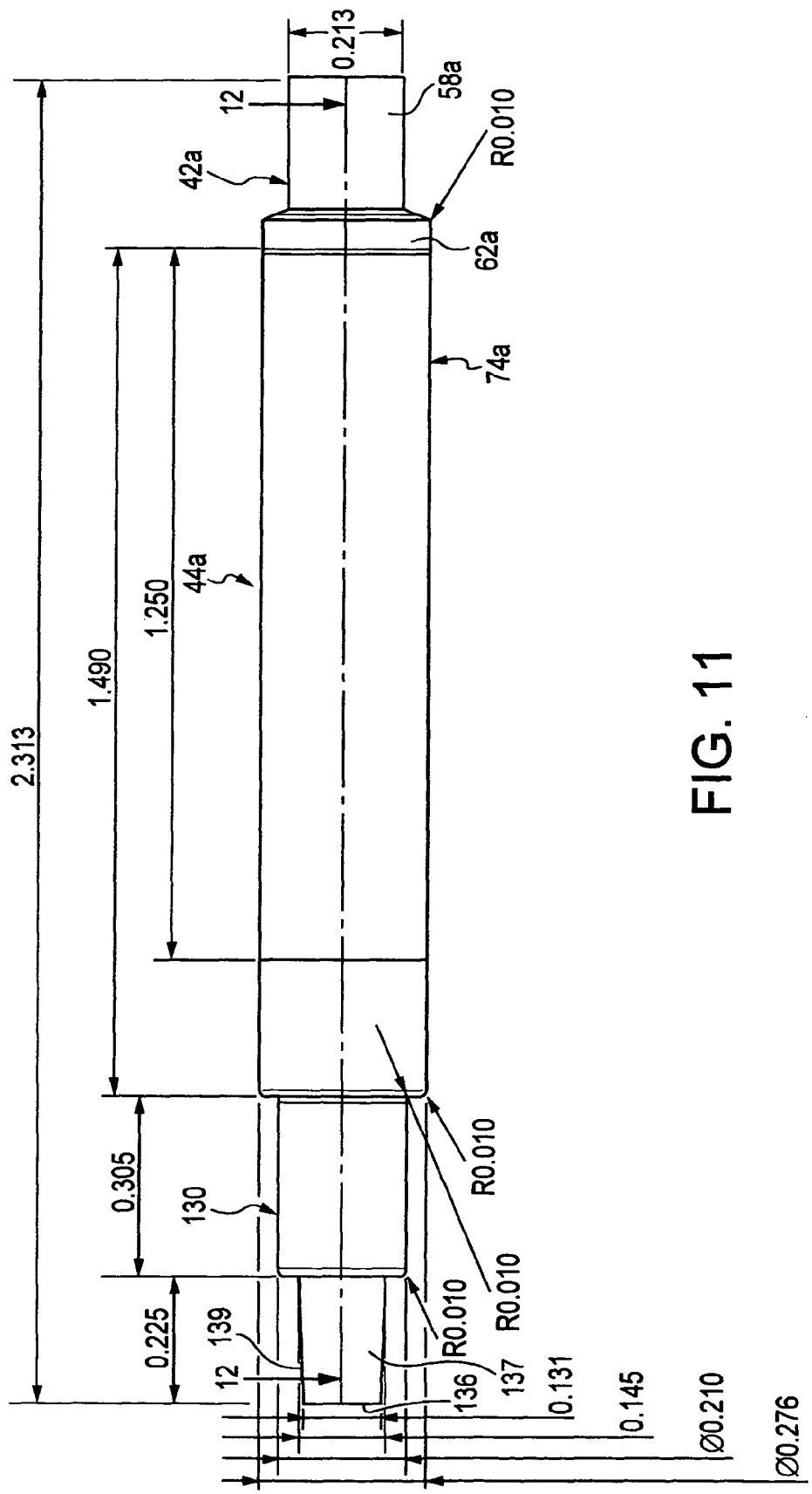
FIG. 11 is a side view showing the dynamic surge suppressor of FIG. 7, with dimensions, in inches, of the components shown herein, in accordance with certain principles of the invention.
Figure 12:
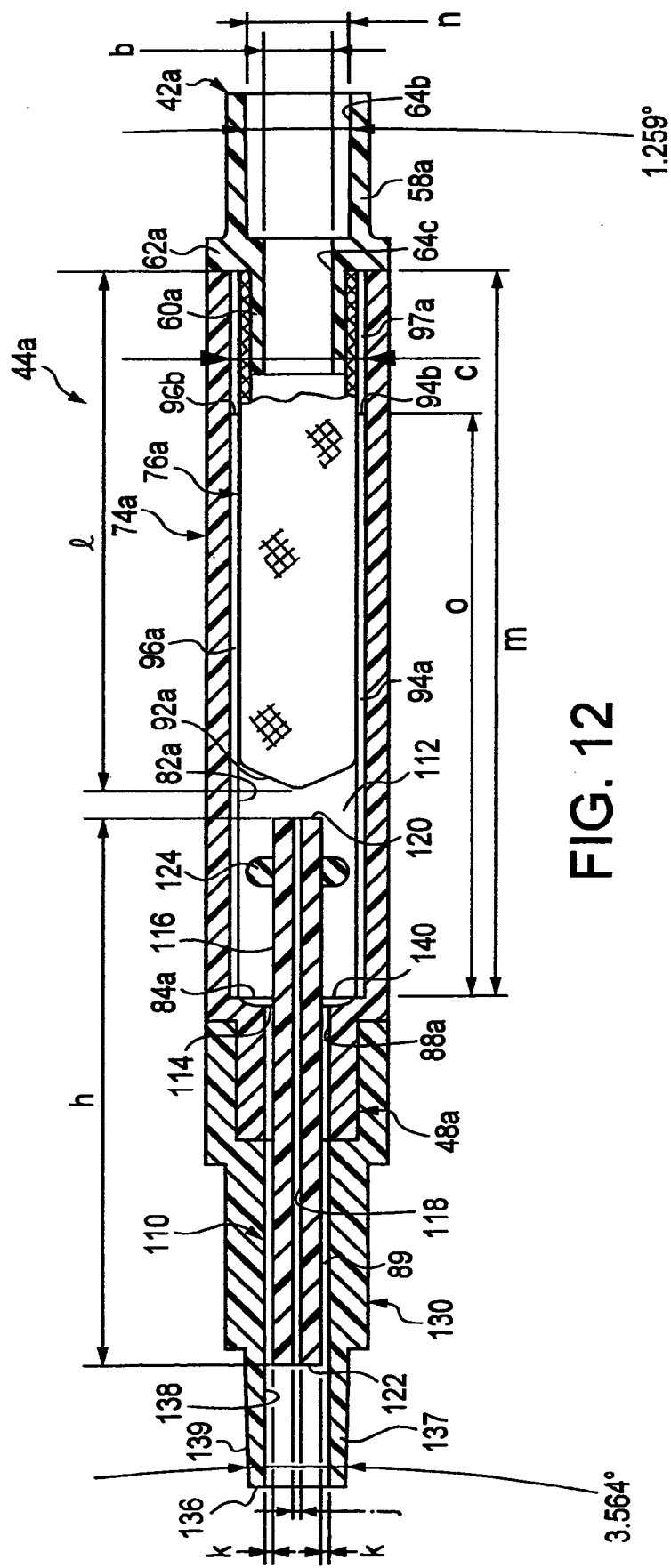
FIG. 12 is a section view showing the dynamic surge suppressor of FIG. 7, with dimensions, in inches, and angular parameters, of the components shown herein, in accordance with certain principles of the invention.

Various dimensions and parameters of the preferred embodiment of filter assembly 44a of the surgical apparatus 10, including the preferred embodiment of the suppressor 110, are shown in FIGS. 11 and 12. In particular, as shown in FIG. 12, the preferred embodiment of the suppressor 110 is formed with the restrictor tube 116, and the inner passage 118, with the tube and the inner passage formed with a preferred axial length "h" in a range between, and including, 0.500 inch and 1.500 inches, and the inner passage formed with a preferred diameter "j" in a range between, and including, 0.005 inch and 1.500 inches. It has been determined these length and diameter dimensions provide the restriction desired for the parameters of operation of the surgical apparatus 10, as described above. Other length and diameter dimensions could be used without departing from the spirit and scope of the invention.

The outer surface of the restrictor tube 116 is spaced from a common inner wall of the aligned passages 88a and 138, which forms the passage 89, and are spaced apart by a distance "k" in a range between 0.005 inch and 0.020 inch. Other space dimensions could be used without departing from the spirit and scope of the invention.

In the preferred embodiment of the surgical apparatus 10, the components of the aspiration system 38 are composed of plastic materials. The input tube 40 and the output tube 46 are standard plastic, flexible tubes of the type typically used in apparatus used in phaco procedures. The input luers 42 and 42a, the filter housings 74 and 74a, the output luers 48 and 48a, and the luer extension 130 are composed of an acrylic material, or of plastics having similar properties. The filters 76 and 76a may be composed of a nylon mesh material. The restrictor tube 116 of the suppressor 110 is composed of polyetheretherketone, a plastic referred to as PEEK. The compliant member 124 is composed of silicon, or a like material.

As shown in FIG. 12, the ribs 94*a* and 96*a* extend from the inner wall 84*a* of the filter housing 74*a* to an end 94*b* and 96*b*, respectively, for an axial length "o" in a range between, and including, 0.850 inch and 1.050 inch. A space 97*a* is thereby provided between the ends 94*b* and 96*b* and the input end of the filter housing 74*a*, so that adjacent outer surface portions of the filter 76*a* are unencumbered by the presence of a rib during the period when the output section 60*a* of the input luer 42*a* is being inserted into the inner passage of the filter.

It is noted that the axial length "l" of the filter 76*a* is in a range between, and including, 0.250 inch and 0.500 inch.

In summary, the surgical apparatus 10 provides a unique filtering facility for near, or complete, elimination of air bubble formation within the aspiration system 38 when operating in an aspiration mode. With no, or minimal, air bubbles in the aspiration line when an occlusion breaks free, the level of the surge in the fluid flow is precluded form dramatically increasing, which enhances the dynamic and quick response by the suppressor 110 to reduce the surge flow rate to a desired level. In addition, the suppressor 110 maintains the fluid flow rate at the desired level during normal operation in the aspiration mode. The surgical apparatus 10 further provides facility for operating in a reflux mode by moving fluid unrestricted through the same aspiration line used during the aspiration mode of operation.

In general, the above-identified embodiments are not to be construed as limiting the breadth of the present invention. Modifications, and other alternative constructions, will be apparent which are within the spirit and scope of the invention as defined in the appended claims.

What is claimed is:

1. A dynamic surge suppressor for use in a phacoemulsification surgical procedure for the removal of lens tissue from an eye of a patient, which comprises:
    a suppressor housing having an inner passage;
    a mesh filter located within a portion of the inner passage of the suppressor housing;
    a tube, having an unobstructed inner passage with a prescribed diameter, located in a portion of the inner passage of the suppressor housing not occupied by the mesh filter;
    the tube unattached to any portion of the suppressor housing, and movable freely independently, and axially, within the inner passage of the suppressor housing; and
    a separate inner passage, independent of the unobstructed inner passage of the tube, formed by a space between an outer surface of the tube and an adjacent portion of an inner wall of the inner passage of the suppressor housing.

2. The dynamic surge suppressor as set forth in claim 1, which further comprises:
    the unobstructed inner passage of the tube having a diameter in a range between, and including, 0.005 inch and 0.015 inch.

3. The dynamic surge suppressor as set forth in claim 1, which further comprises:
    a distance of the space between the outer surface of the tube and the adjacent portion of the inner wall of the inner passage of the surge suppressor being in a range between, and including, 0.005 inch and 0.0020 inch.

4. The dynamic surge suppressor as set forth in claim 1, which further comprises:
    the tube has an axial length of between, and including, 0.500 inch to 1.500 inches.

5. The dynamic surge suppressor as set forth in claim 1, which further comprises:
    a force responder attached to the tube for facilitating axial movement of the tube in response to a force of fluid flowing in either axial direction within the inner passage of the suppressor housing.

6. The dynamic surge suppressor as set forth in claim 1, which further comprises:
    a compliant force responder attached to the tube for blocking the separate inner passage in response to the force of fluid flowing in a prescribed direction within the inner passage of the suppressor housing.

7. The dynamic surge suppressor as set forth in claim 1, which further comprises:
    a force-responder limiter attached to the tube for engaging structure of the suppressor housing to limit the axial movement of the tube.

8. The dynamic surge suppressor as set forth in claim 1, which further comprises:
    the space surrounds the outer surface of the tube.

9. The dynamic surge suppressor as set forth in claim 1, which further comprises:
    the unobstructed inner passage of the tube and the separate inner passage located in a common portion of the inner passage of the suppressor housing such that fluid flowing through the common portion will be separated, with a portion of the separated fluid flowing though the unobstructed inner passage and a remainder portion flowing through the separate inner passage.

10. The dynamic surge suppressor as set forth in claim 9, which further comprises:
    a force responder attached to the tube for facilitating axial movement of the tube in either axial direction in response to an increase or decrease in the level of a force, from a prescribed level of force, of fluid flowing in either axial direction within the inner passage of the suppressor housing.

11. The dynamic surge suppressor as set forth in claim 10, which further comprises:
    the force responder responds to changes in the force of fluid flowing in the inner passage of the suppressor housing to increase or decrease the rate of fluid flowing through the separate inner passage.

12. The dynamic surge suppressor as set forth in claim 9, which further comprises:
    a compliant force responder attached to the tube for blocking the separate inner passage in response to an increase, from a prescribed level, in a level of the force of fluid flowing in a prescribed direction within the inner passage of the suppressor housing such that all of the fluid in the inner passage of the suppressor housing flows through the unobstructed inner passage of the tube.

13. The dynamic surge suppressor as set forth in claim 12, which further comprises:
    the unobstructed inner passage being formed with a fixed restrictive diameter which limits the rate of flow of the fluid through the inner passage of the suppressor housing during a period when the separate inner passage is blocked.

14. The dynamic surge suppressor as set forth in claim 13, which further comprises:
    the fixed restrictive diameter of the unobstructed inner passage being in a range between, and including, 0.005 inch to 0.020 inch.

15. The dynamic surge suppressor as set forth in claim 9, which further comprises:
   a force-responder limiter attached to the tube for engaging structure of the suppressor housing to limit the axial movement of the tube.

16. The dynamic surge suppressor as set forth in claim 9, which further comprises:
   a force responder attached to the tube and being movable in either axial direction, upon movement of the tube, between a location of least restriction to the flow of the fluid in the inner passage of the suppressor housing and a location of maximum restriction to the flow of fluid in the inner passage.

17. The dynamic surge suppressor as set forth in claim 16, which further comprises:
   the force responder being locatable at any position between the locations of least restriction and maximum restriction.

18. The dynamic surge suppressor as set forth in claim 1, which further comprises:
   the space defines a volume of the separate inner passage through which fluid flows, with the volume being altered upon axial movement of the tube.

19. A dynamic surge suppressor for use in a phacoemulsification surgical procedure for the removal of lens tissue from an eye of a patient, which comprises:
   a suppressor housing having an inner passage;
   a tube, having an unobstructed inner passage with a prescribed diameter, located in a portion of the inner passage of the suppressor housing;
   the tube unattached to any portion of the suppressor housing, and movable freely, independently, and axially, within the inner passage of the suppressor housing; and
   a separate inner passage, independent of the unobstructed inner passage of the tube, formed by a space between an outer surface of the tube and an adjacent portion of an inner wall of the inner passage of the suppressor housing.

20. The dynamic surge suppressor as set forth in claim 19, which further comprises:
   a compliant force responder attached to the tube for blocking the separate inner passage in response to an increase, from a prescribed level, in a level of the force of fluid flowing in a prescribed direction within the inner passage of the suppressor housing such that all of the fluid in the inner passage of the suppressor housing flows through the unobstructed inner passage of the tube.

21. The dynamic surge suppressor as set forth in claim 19, which further comprises:
   a force-responder limiter attached to the tube for engaging structure of the suppressor housing to limit the axial movement of the tube.

22. The dynamic surge suppressor as set forth in claim 19, which further comprises:
   a force responder attached to the tube and being movable in either axial direction, upon movement of the tube, between a location of least restriction to the flow of the fluid in the inner passage of the suppressor housing and a location of maximum restriction to the flow of fluid in the inner passage.

23. The dynamic surge suppressor as set forth in claim 22, which further comprises:
   the force responder being locatable at any position between the locations of least restriction and maximum restriction.

\* \* \* \* \*